(12) United States Patent
Demarais et al.

(10) Patent No.: US 8,774,913 B2
(45) Date of Patent: Jul. 8, 2014

(54) METHODS AND APPARATUS FOR INTRAVASCULARY-INDUCED NEUROMODULATION

(75) Inventors: Denise Demarais, Los Gatos, CA (US); Hanson Gifford, III, Woodside, CA (US); Mark Deem, Mountain View, CA (US); Douglas Sutton, Pacifica, CA (US); Erik Thai, San Jose, CA (US); Benjamin J. Clark, Redwood City, CA (US); Nicolas Zadno, Fremont, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 11/599,649

(22) Filed: Nov. 14, 2006

(65) Prior Publication Data

US 2007/0129760 A1    Jun. 7, 2007

Related U.S. Application Data

(63) Continuation-in-part of application No. 11/363,867, filed on Feb. 27, 2006, now Pat. No. 7,620,451, which is a continuation-in-part of application No. 11/129,765, filed on May 13, 2005, now Pat. No. 7,653,438, and a continuation-in-part of application No. 10/408,665, filed on Apr. 8, 2003, now Pat. No. 7,162,303, said application No. 11/599,649 is a continuation-in-part of application No. 11/189,563, filed on Jul. 25, 2005, now Pat. No. 8,145,316, and a continuation-in-part of application No. 10/900,199, filed on Jul. 28, 2004, now Pat. No. 6,978,174, said application No. 11/599,649 is a continuation-in-part of application No. 11/403,329, filed on Apr. 13, 2006, now Pat. No. 8,131,371, said application No. 11/403,329 is a continuation-in-part of application No. 11/266,933, filed on Nov. 4, 2005, now Pat. No. 7,551,057, said application No. 11/599,649 is a continuation-in-part of application No. 11/504,117, filed on Aug. 14, 2006, now Pat. No. 7,617,005, which is a continuation-in-part of application No. 10/408,665, filed on Apr. 8, 2003, now Pat. No. 7,162,303.

(60) Provisional application No. 60/813,589, filed on Dec. 29, 2005, provisional application No. 60/616,254, filed on Oct. 5, 2004, provisional application No. 60/624,793, filed on Nov. 2, 2004, provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61N 1/05* (2006.01)
(52) U.S. Cl.
USPC ............................................................ 607/3
(58) Field of Classification Search
USPC ........................................................ 607/2, 3
See application file for complete search history.

(56) References Cited

U.S. PATENT DOCUMENTS 2,130,758 A   9/1938  Rose
2,276,995 A   3/1942  Milinowski
(Continued)

FOREIGN PATENT DOCUMENTS

CN   201356648   12/2009
CN   201469401    5/2010
(Continued)

OTHER PUBLICATIONS

U.S. Appl. No. 10/408,665, filed Apr. 8, 2003, Levin et al.
(Continued)

*Primary Examiner* — Eric D. Bertram

(57) ABSTRACT

Methods and apparatus are provided for intravascularly-induced neuromodulation or denervation. Neuromodulation may be achieved via direct and/or via indirect application of energy or neuromodulatory agents to target neural matter, or to vascular structures that support the target neural matter. In some embodiments, parameters of the target neural matter, of non-target tissue, or of the apparatus may be monitored via one or more sensors for controlling the neuromodulation or denervation. Such monitoring data optionally may be utilized for feedback control of the neuromodulation or denervation.

15 Claims, 6 Drawing Sheets

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et at |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,935,348 A | 1/1976 | Smith |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany |
| 4,071,033 A | 1/1978 | Nawracaj et al. |
| 4,105,017 A | 8/1978 | Ryaby et al. |
| 4,141,365 A | 2/1979 | Fischell et al. |
| 4,154,246 A | 5/1979 | LeVeen |
| 4,169,464 A | 10/1979 | Obrez |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,419,819 A | 12/1983 | Dickhudt et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,531,943 A | 7/1985 | Van Tassel et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,660,571 A | 4/1987 | Hess et al. |
| 4,671,286 A | 6/1987 | Renault |
| 4,674,482 A | 6/1987 | Waltonen et al. |
| 4,692,147 A | 9/1987 | Duggan |
| 4,706,671 A | 11/1987 | Weinrib |
| 4,709,698 A | 12/1987 | Johnston et al. |
| 4,715,852 A | 12/1987 | Reinicke et al. |
| 4,774,967 A | 10/1988 | Zanakis |
| 4,781,682 A | 11/1988 | Patel |
| 4,791,931 A | 12/1988 | Slate |
| 4,796,643 A | 1/1989 | Nakazawa et al. |
| 4,816,016 A | 3/1989 | Schulte et al. |
| 4,819,661 A | 4/1989 | Heil, Jr. et al. |
| 4,852,573 A | 8/1989 | Kennedy |
| 4,860,769 A | 8/1989 | Fogarty et al. |
| 4,865,845 A | 9/1989 | Eckenhoff et al. |
| 4,921,484 A | 5/1990 | Hillstead |
| 4,957,118 A | 9/1990 | Erlebacher |
| 4,961,377 A | 10/1990 | Bando et al. |
| 4,966,597 A | 10/1990 | Cosman |
| 4,976,711 A | 12/1990 | Parins et al. |
| 4,979,511 A | 12/1990 | Terry, Jr. |
| 4,981,146 A | 1/1991 | Bertolucci |
| 4,995,868 A | 2/1991 | Brazier |
| 4,998,532 A | 3/1991 | Griffith |
| 5,002,067 A | 3/1991 | Berthelsen et al. |
| 5,006,119 A | 4/1991 | Acker et al. |
| 5,011,488 A | 4/1991 | Ginsburg |
| 5,014,699 A | 5/1991 | Pollack et al. |
| 5,016,808 A | 5/1991 | Heil, Jr. et al. |
| 5,019,034 A | 5/1991 | Weaver et al. |
| 5,052,998 A | 10/1991 | Zimmon |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,071,407 A | 12/1991 | Termin et al. |
| 5,078,717 A | 1/1992 | Parins et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,133,365 A | 7/1992 | Heil, Jr. et al. |
| 5,137,727 A | 8/1992 | Eckenhoff |
| 5,156,151 A | 10/1992 | Imran |
| 5,163,928 A | 11/1992 | Hobbs et al. |
| 5,188,602 A | 2/1993 | Nichols |
| 5,188,619 A | 2/1993 | Myers |
| 5,188,837 A | 2/1993 | Domb |
| 5,190,540 A | 3/1993 | Lee |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,209,723 A | 5/1993 | Twardowski et al. |
| 5,213,098 A | 5/1993 | Bennett et al. |
| 5,215,086 A | 6/1993 | Terry, Jr. et al. |
| 5,228,442 A | 7/1993 | Imran |
| 5,231,988 A | 8/1993 | Wernicke et al. |
| 5,234,692 A | 8/1993 | Magruder et al. |
| 5,234,693 A | 8/1993 | Magruder et al. |
| 5,239,999 A | 8/1993 | Imran |
| 5,249,585 A | 10/1993 | Turner et al. |
| 5,251,634 A | 10/1993 | Weinberg |
| 5,251,643 A | 10/1993 | Osypka |
| 5,263,480 A | 11/1993 | Wernicke et al. |
| 5,263,492 A | 11/1993 | Voyce |
| 5,263,493 A | 11/1993 | Avitall |
| 5,269,303 A | 12/1993 | Wernicke et al. |
| 5,279,299 A | 1/1994 | Imran |
| 5,282,468 A | 2/1994 | Klepinski |
| 5,282,785 A | 2/1994 | Shapland et al. |
| 5,286,254 A | 2/1994 | Shapland et al. |
| 5,296,510 A | 3/1994 | Yamada et al. |
| 5,299,569 A | 4/1994 | Wernicke et al. |
| 5,300,068 A | 4/1994 | Rosar et al. |
| 5,300,099 A | 4/1994 | Rudie |
| 5,304,120 A | 4/1994 | Crandell et al. |
| 5,304,206 A | 4/1994 | Baker |
| 5,308,323 A | 5/1994 | Sogawa et al. |
| 5,317,155 A | 5/1994 | King |
| 5,318,525 A | 6/1994 | West et al. |
| 5,324,255 A | 6/1994 | Passafaro et al. |
| 5,324,284 A | 6/1994 | Imran |
| 5,324,316 A | 6/1994 | Schulman et al. |
| 5,327,905 A | 7/1994 | Avitall |
| 5,329,923 A | 7/1994 | Lundquist |
| 5,334,193 A | 8/1994 | Nardella |
| 5,335,657 A | 8/1994 | Terry, Jr. et al. |
| 5,338,662 A | 8/1994 | Sadri |
| 5,345,031 A | 9/1994 | Schwartz et al. |
| 5,345,936 A | 9/1994 | Pomeranz et al. |
| 5,351,394 A | 10/1994 | Weinberg |
| 5,354,297 A | 10/1994 | Avitall |
| 5,358,514 A | 10/1994 | Schulman et al. |
| 5,365,926 A | 11/1994 | Desai |
| 5,368,591 A | 11/1994 | Lennox et al. |
| 5,370,680 A | 12/1994 | Proctor |
| 5,383,856 A | 1/1995 | Bersin |
| 5,387,233 A | 2/1995 | Alferness et al. |
| 5,389,069 A | 2/1995 | Weaver |
| 5,397,304 A | 3/1995 | Truckai |
| 5,397,308 A | 3/1995 | Ellis et al. |
| 5,397,338 A | 3/1995 | Grey et al. |
| 5,397,339 A | 3/1995 | Desai |

(56) References Cited

U.S. PATENT DOCUMENTS

| | | |
|---|---|---|
| 5,399,164 A | 3/1995 | Snoke et al. |
| 5,400,784 A | 3/1995 | Durand et al. |
| 5,405,367 A | 4/1995 | Schulman et al. |
| 5,405,374 A | 4/1995 | Stein |
| 5,411,546 A | 5/1995 | Bowald et al. |
| 5,421,349 A | 6/1995 | Rodriguez et al. |
| 5,423,744 A | 6/1995 | Gencheff et al. |
| 5,425,364 A | 6/1995 | Imran |
| 5,429,634 A | 7/1995 | Narciso, Jr. |
| 5,433,739 A | 7/1995 | Sluijter et al. |
| 5,439,440 A | 8/1995 | Hofmann |
| 5,441,483 A | 8/1995 | Avitall |
| 5,454,782 A | 10/1995 | Perkins |
| 5,454,809 A | 10/1995 | Janssen |
| 5,458,568 A | 10/1995 | Racchini et al. |
| 5,458,585 A | 10/1995 | Salmon et al. |
| 5,458,626 A | 10/1995 | Krause |
| 5,458,631 A | 10/1995 | Xavier |
| 5,462,545 A | 10/1995 | Wang et al. |
| 5,465,717 A | 11/1995 | Imran et al. |
| 5,470,352 A | 11/1995 | Rappaport |
| 5,472,406 A | 12/1995 | de la Torre et al. |
| 5,476,495 A | 12/1995 | Kordis et al. |
| 5,476,498 A | 12/1995 | Ayers |
| 5,477,856 A | 12/1995 | Lundquist |
| 5,478,303 A | 12/1995 | Foley-Nolan et al. |
| 5,484,400 A | 1/1996 | Edwards et al. |
| 5,487,385 A | 1/1996 | Avitall |
| 5,487,757 A | 1/1996 | Truckai et al. |
| 5,494,822 A | 2/1996 | Sadri |
| 5,496,311 A | 3/1996 | Abele et al. |
| 5,497,774 A | 3/1996 | Swartz et al. |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,743 A | 4/1996 | Edwards et al. |
| 5,507,791 A | 4/1996 | Sit'ko |
| 5,509,909 A | 4/1996 | Moy |
| 5,523,092 A | 6/1996 | Hanson et al. |
| 5,529,820 A | 6/1996 | Nomi et al. |
| 5,531,778 A | 7/1996 | Maschino et al. |
| 5,540,679 A | 7/1996 | Fram et al. |
| 5,540,730 A | 7/1996 | Terry, Jr. et al. |
| 5,540,734 A | 7/1996 | Zabara |
| 5,545,193 A | 8/1996 | Fleischman et al. |
| 5,545,200 A | 8/1996 | West et al. |
| 5,545,475 A | 8/1996 | Korleski |
| 5,549,661 A | 8/1996 | Kordis et al. |
| 5,553,611 A | 9/1996 | Budd et al. |
| 5,558,643 A | 9/1996 | Samson et al. |
| 5,560,360 A | 10/1996 | Filler et al. |
| 5,564,440 A | 10/1996 | Swartz et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,575,766 A | 11/1996 | Swartz et al. |
| 5,575,810 A | 11/1996 | Swanson et al. |
| 5,582,609 A | 12/1996 | Swanson et al. |
| 5,584,863 A | 12/1996 | Rauch et al. |
| 5,589,192 A | 12/1996 | Okabe et al. |
| 5,591,132 A | 1/1997 | Carrie |
| 5,599,345 A | 2/1997 | Edwards et al. |
| 5,609,151 A | 3/1997 | Mulier et al. |
| 5,617,854 A | 4/1997 | Munsif |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,628,775 A | 5/1997 | Jackson et al. |
| 5,634,462 A | 6/1997 | Tyler et al. |
| 5,634,899 A | 6/1997 | Shapland et al. |
| 5,636,634 A | 6/1997 | Kordis et al. |
| 5,637,090 A | 6/1997 | McGee et al. |
| 5,642,736 A | 7/1997 | Avitall |
| 5,672,174 A | 9/1997 | Gough et al. |
| 5,676,662 A | 10/1997 | Fleischhacker et al. |
| 5,680,860 A | 10/1997 | Imran |
| 5,681,280 A | 10/1997 | Rusk et al. |
| 5,687,723 A | 11/1997 | Avitall |
| 5,688,266 A | 11/1997 | Edwards et al. |
| 5,689,877 A | 11/1997 | Grill, Jr. et al. |
| 5,690,611 A | 11/1997 | Swartz et al. |
| 5,690,691 A | 11/1997 | Chen et al. |
| 5,697,928 A | 12/1997 | Walcott et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,709,874 A | 1/1998 | Hanson et al. |
| 5,711,326 A | 1/1998 | Thies et al. |
| 5,713,847 A | 2/1998 | Howard, III et al. |
| 5,715,818 A | 2/1998 | Swartz et al. |
| 5,722,401 A | 3/1998 | Pietroski et al. |
| 5,723,001 A | 3/1998 | Pilla et al. |
| 5,725,512 A | 3/1998 | Swartz et al. |
| 5,725,563 A | 3/1998 | Klotz et al. |
| 5,727,555 A | 3/1998 | Chait |
| 5,728,396 A | 3/1998 | Peery et al. |
| 5,730,127 A | 3/1998 | Avitall |
| 5,730,741 A | 3/1998 | Horzewski et al. |
| 5,747,060 A | 5/1998 | Sackler et al. |
| 5,755,750 A | 5/1998 | Petruska et al. |
| 5,755,760 A | 5/1998 | Maguire et al. |
| 5,755,761 A | 5/1998 | Obino |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,249 A | 9/1998 | Qin et al. |
| 5,807,306 A | 9/1998 | Shapland et al. |
| 5,807,395 A | 9/1998 | Mulier et al. |
| 5,810,802 A | 9/1998 | Panescu et al. |
| 5,814,028 A | 9/1998 | Swartz et al. |
| 5,814,079 A | 9/1998 | Kieval |
| 5,823,955 A | 10/1998 | Kuck et al. |
| 5,824,087 A | 10/1998 | Aspden et al. |
| 5,827,268 A | 10/1998 | Laufer |
| 5,836,935 A | 11/1998 | Ashton et al. |
| RE35,987 E | 12/1998 | Harris et al. |
| 5,842,984 A | 12/1998 | Avitall |
| 5,843,069 A | 12/1998 | Butler et al. |
| 5,846,355 A | 12/1998 | Spencer et al. |
| 5,860,920 A | 1/1999 | McGee et al. |
| 5,860,922 A | 1/1999 | Gordon et al. |
| 5,860,974 A | 1/1999 | Abele |
| 5,861,021 A | 1/1999 | Thome et al. |
| 5,865,787 A | 2/1999 | Shapland et al. |
| 5,865,815 A | 2/1999 | Tihon |
| 5,871,444 A | 2/1999 | Ouchi |
| 5,871,449 A | 2/1999 | Brown |
| 5,871,523 A | 2/1999 | Fleischman et al. |
| 5,871,531 A | 2/1999 | Struble |
| 5,873,865 A | 2/1999 | Horzewski et al. |
| 5,879,295 A | 3/1999 | Li et al. |
| 5,882,346 A | 3/1999 | Pomeranz et al. |
| 5,891,181 A | 4/1999 | Zhu |
| 5,893,885 A | 4/1999 | Webster et al. |
| 5,906,636 A | 5/1999 | Casscells, III et al. |
| 5,906,817 A | 5/1999 | Moullier et al. |
| 5,910,129 A | 6/1999 | Koblish et al. |
| 5,913,876 A | 6/1999 | Taylor et al. |
| 5,916,154 A | 6/1999 | Hobbs et al. |
| 5,916,178 A | 6/1999 | Noone et al. |
| 5,916,214 A | 6/1999 | Cosio et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,931,848 A | 8/1999 | Saadat |
| 5,935,075 A | 8/1999 | Casscells et al. |
| 5,935,102 A | 8/1999 | Bowden et al. |
| 5,938,694 A | 8/1999 | Jaraczewski et al. |

(56) References Cited

U.S. PATENT DOCUMENTS

| | | |
|---|---|---|
| 5,941,823 A | 8/1999 | Chait |
| 5,944,710 A | 8/1999 | Dev et al. |
| 5,951,471 A | 9/1999 | de la Rama et al. |
| 5,954,719 A | 9/1999 | Chen et al. |
| 5,957,961 A | 9/1999 | Maguire et al. |
| 5,968,085 A | 10/1999 | Morris et al. |
| 5,972,026 A | 10/1999 | Laufer et al. |
| 5,980,516 A | 11/1999 | Mulier et al. |
| 5,983,131 A | 11/1999 | Weaver et al. |
| 5,983,141 A | 11/1999 | Sluijter et al. |
| 5,984,907 A | 11/1999 | McGee et al. |
| 5,993,462 A | 11/1999 | Pomeranz et al. |
| 5,997,526 A | 12/1999 | Giba et al. |
| 6,004,269 A | 12/1999 | Crowley et al. |
| 6,004,348 A | 12/1999 | Banas et al. |
| 6,006,134 A | 12/1999 | Hill et al. |
| 6,009,877 A | 1/2000 | Edwards |
| 6,010,613 A | 1/2000 | Walters et al. |
| 6,012,457 A | 1/2000 | Lesh |
| 6,024,740 A | 2/2000 | Lesh et al. |
| 6,026,326 A | 2/2000 | Bardy |
| 6,032,077 A | 2/2000 | Pomeranz |
| 6,041,252 A | 3/2000 | Walker et al. |
| 6,042,578 A | 3/2000 | Dinh et al. |
| 6,042,580 A | 3/2000 | Simpson |
| 6,048,329 A | 4/2000 | Thompson et al. |
| 6,049,737 A | 4/2000 | Simpson et al. |
| 6,051,017 A | 4/2000 | Loeb et al. |
| 6,058,328 A | 5/2000 | Levine et al. |
| 6,058,331 A | 5/2000 | King |
| 6,064,902 A | 5/2000 | Haissaguerre et al. |
| 6,066,134 A | 5/2000 | Eggers et al. |
| 6,071,729 A | 6/2000 | Jeffries et al. |
| 6,073,048 A | 6/2000 | Kieval et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,077,227 A | 6/2000 | Miesel et al. |
| 6,078,840 A | 6/2000 | Stokes |
| 6,078,841 A | 6/2000 | Kuzma |
| 6,086,527 A | 7/2000 | Talpade |
| 6,090,104 A | 7/2000 | Webster, Jr. |
| 6,091,995 A | 7/2000 | Ingle et al. |
| 6,094,596 A | 7/2000 | Morgan |
| 6,096,036 A | 8/2000 | Bowe et al. |
| 6,099,524 A | 8/2000 | Lipson et al. |
| 6,106,522 A | 8/2000 | Fleischman et al. |
| 6,110,192 A | 8/2000 | Ravenscroft et al. |
| 6,117,101 A | 9/2000 | Diederich et al. |
| 6,122,548 A | 9/2000 | Starkebaum et al. |
| 6,123,718 A | 9/2000 | Tu et al. |
| 6,125,302 A | 9/2000 | Kuzma |
| 6,129,750 A | 10/2000 | Tockman et al. |
| 6,132,456 A | 10/2000 | Sommer et al. |
| 6,135,999 A | 10/2000 | Fanton et al. |
| 6,146,380 A | 11/2000 | Racz et al. |
| 6,146,381 A | 11/2000 | Bowe et al. |
| 6,161,048 A | 12/2000 | Sluijter et al. |
| 6,161,049 A | 12/2000 | Rudie et al. |
| 6,164,283 A | 12/2000 | Lesh |
| 6,171,306 B1 | 1/2001 | Swanson |
| 6,178,349 B1 | 1/2001 | Kieval |
| 6,190,353 B1 | 2/2001 | Makower et al. |
| 6,190,356 B1 | 2/2001 | Bersin |
| 6,192,889 B1 | 2/2001 | Morrish |
| 6,197,021 B1 | 3/2001 | Panescu et al. |
| 6,205,361 B1 | 3/2001 | Kuzma et al. |
| 6,208,894 B1 | 3/2001 | Schulman et al. |
| 6,214,002 B1 | 4/2001 | Fleischman et al. |
| 6,214,032 B1 | 4/2001 | Loeb et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,238,702 B1 | 5/2001 | Berde et al. |
| 6,245,026 B1 | 6/2001 | Campbell et al. |
| 6,246,912 B1 | 6/2001 | Sluijter |
| 6,246,914 B1 | 6/2001 | de la Rama et al. |
| 6,251,109 B1 | 6/2001 | Hassett et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,270,496 B1 | 8/2001 | Bowe et al. |
| 6,272,377 B1 | 8/2001 | Sweeney et al. |
| 6,272,383 B1 | 8/2001 | Grey et al. |
| 6,273,886 B1 | 8/2001 | Edwards |
| 6,280,377 B1 | 8/2001 | Talpade |
| 6,280,441 B1 | 8/2001 | Ryan |
| 6,283,960 B1 | 9/2001 | Ashley |
| 6,287,304 B1 | 9/2001 | Eggers et al. |
| 6,287,306 B1 | 9/2001 | Kroll et al. |
| 6,287,608 B1 | 9/2001 | Levin et al. |
| 6,292,695 B1 * | 9/2001 | Webster et al. ............... 607/14 |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,308,090 B1 | 10/2001 | Tu et al. |
| 6,312,425 B1 | 11/2001 | Simpson et al. |
| 6,314,325 B1 | 11/2001 | Fitz |
| 6,319,250 B1 | 11/2001 | Falwell et al. |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,364,904 B1 | 4/2002 | Smith |
| 6,366,808 B1 | 4/2002 | Schroeppel et al. |
| 6,366,815 B1 | 4/2002 | Haugland et al. |
| 6,385,472 B1 | 5/2002 | Hall et al. |
| 6,393,324 B2 | 5/2002 | Gruzdowich et al. |
| 6,400,982 B2 | 6/2002 | Sweeney et al. |
| 6,405,067 B1 | 6/2002 | Mest et al. |
| 6,405,079 B1 | 6/2002 | Ansarinia |
| 6,405,732 B1 | 6/2002 | Edwards et al. |
| 6,409,742 B1 | 6/2002 | Fulton, III et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,430,426 B2 | 8/2002 | Avitall |
| 6,438,423 B1 | 8/2002 | Rezai et al. |
| 6,442,415 B1 | 8/2002 | Bis et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,451,045 B1 | 9/2002 | Walker et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,480,747 B2 | 11/2002 | Schmidt |
| 6,482,619 B1 | 11/2002 | Rubinsky et al. |
| 6,488,679 B1 | 12/2002 | Swanson et al. |
| 6,496,737 B2 | 12/2002 | Rudie et al. |
| 6,500,172 B1 | 12/2002 | Panescu et al. |
| 6,500,174 B1 | 12/2002 | Maguire et al. |
| 6,506,189 B1 | 1/2003 | Rittman et al. |
| 6,508,774 B1 | 1/2003 | Acker et al. |
| 6,511,492 B1 | 1/2003 | Rosenbluth et al. |
| 6,514,226 B1 | 2/2003 | Levin et al. |
| 6,514,249 B1 | 2/2003 | Maguire et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,527,739 B1 | 3/2003 | Bigus et al. |

(56) References Cited

U.S. PATENT DOCUMENTS

| | | |
|---|---|---|
| 6,529,756 B1 | 3/2003 | Phan et al. |
| 6,530,935 B2 | 3/2003 | Wensel et al. |
| 6,534,081 B2 | 3/2003 | Goldenheim et al. |
| 6,536,949 B1 | 3/2003 | Heuser |
| 6,540,734 B1 | 4/2003 | Newton et al. |
| 6,542,781 B1 | 4/2003 | Koblish et al. |
| 6,546,280 B2 | 4/2003 | Osborne |
| 6,554,774 B1 | 4/2003 | Miele |
| 6,562,031 B2 | 5/2003 | Chandrasekaran et al. |
| 6,562,034 B2 | 5/2003 | Edwards et al. |
| 6,564,096 B2 | 5/2003 | Mest |
| 6,571,127 B1 | 5/2003 | Ben-Haim et al. |
| 6,572,612 B2 | 6/2003 | Stewart et al. |
| 6,592,567 B1 | 7/2003 | Levin et al. |
| 6,592,581 B2 | 7/2003 | Bowe |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni et al. |
| 6,602,242 B1 | 8/2003 | Fung et al. |
| 6,605,061 B2 | 8/2003 | VanTassel et al. |
| 6,605,084 B2 | 8/2003 | Acker et al. |
| 6,605,087 B2 | 8/2003 | Swartz et al. |
| 6,607,520 B2 | 8/2003 | Keane |
| 6,610,046 B1 | 8/2003 | Usami et al. |
| 6,610,083 B2 | 8/2003 | Keller et al. |
| 6,611,720 B2 | 8/2003 | Hata et al. |
| 6,613,045 B1 | 9/2003 | Laufer et al. |
| 6,613,046 B1 | 9/2003 | Jenkins et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,623,515 B2 | 9/2003 | Mulier et al. |
| 6,628,976 B1 | 9/2003 | Fuimaono et al. |
| 6,635,054 B2 | 10/2003 | Fjield et al. |
| 6,638,278 B2 | 10/2003 | Falwell et al. |
| 6,652,517 B1 | 11/2003 | Hall et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,490 B1 | 2/2004 | Edwards |
| 6,692,738 B2 | 2/2004 | MacLaughlin et al. |
| 6,697,670 B2 | 2/2004 | Chomenky et al. |
| 6,702,811 B2 | 3/2004 | Stewart et al. |
| 6,711,444 B2 | 3/2004 | Koblish |
| 6,716,207 B2 | 4/2004 | Farnholtz |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,745,080 B2 | 6/2004 | Koblish |
| 6,748,255 B2 | 6/2004 | Fuimaono et al. |
| 6,749,598 B1 | 6/2004 | Keren et al. |
| 6,752,805 B2 | 6/2004 | Maguire et al. |
| 6,758,830 B1 | 7/2004 | Schaer et al. |
| 6,773,433 B2 | 8/2004 | Stewart et al. |
| 6,780,181 B2 | 8/2004 | Kroll et al. |
| 6,780,183 B2 | 8/2004 | Jimenez, Jr. et al. |
| 6,786,904 B2 | 9/2004 | Doscher et al. |
| 6,795,728 B2 | 9/2004 | Chornenky et al. |
| 6,802,840 B2 | 10/2004 | Chin et al. |
| 6,817,999 B2 | 11/2004 | Berube et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,882,886 B1 | 4/2005 | Witte et al. |
| 6,885,888 B2 | 4/2005 | Rezai |
| 6,890,329 B2 | 5/2005 | Carroll et al. |
| 6,893,438 B2 | 5/2005 | Hall et al. |
| 6,899,711 B2 | 5/2005 | Stewart et al. |
| 6,905,510 B2 | 6/2005 | Saab |
| 6,909,920 B2 | 6/2005 | Lokhoff et al. |
| 6,916,656 B2 | 7/2005 | Walters et al. |
| 6,923,808 B2 | 8/2005 | Taimisto |
| 6,926,669 B1 | 8/2005 | Stewart et al. |
| 6,926,716 B2 | 8/2005 | Baker et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,941,953 B2 | 9/2005 | Feld et al. |
| 6,949,097 B2 | 9/2005 | Stewart et al. |
| 6,958,060 B2 | 10/2005 | Mathiesen et al. |
| 6,960,206 B2 | 11/2005 | Keane |
| 6,960,207 B2 | 11/2005 | Vanney et al. |
| 6,964,660 B2 | 11/2005 | Maguire et al. |
| 6,969,388 B2 | 11/2005 | Goldman et al. |
| 6,972,013 B1 | 12/2005 | Zhang et al. |
| 6,972,016 B2 | 12/2005 | Hill, III et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,013,169 B2 | 3/2006 | Bowe |
| 7,013,170 B2 | 3/2006 | Bowe |
| 7,054,685 B2 | 5/2006 | Dimmer et al. |
| 7,058,456 B2 | 6/2006 | Pierce |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,104,988 B2 | 9/2006 | Altman et al. |
| 7,110,828 B2 | 9/2006 | Kolberg et al. |
| 7,115,134 B2 | 10/2006 | Chambers |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,171,275 B2 | 1/2007 | Hata et al. |
| 7,201,738 B1 | 4/2007 | Bengmark |
| 7,211,082 B2 | 5/2007 | Hall et al |
| 7,254,451 B2 | 8/2007 | Seifert et al. |
| 7,285,119 B2 | 10/2007 | Stewart et al. |
| 7,291,146 B2 | 11/2007 | Steinke et al. |
| 7,311,705 B2 | 12/2007 | Sra |
| 7,373,204 B2 | 5/2008 | Gelfand et al. |
| 7,435,248 B2 | 10/2008 | Taimisto et al. |
| 7,444,183 B2 | 10/2008 | Knudson et al. |
| 7,517,349 B2 | 4/2009 | Truckai et al. |
| 7,526,343 B2 | 4/2009 | Peterson et al. |
| 7,542,808 B1 | 6/2009 | Peterson et al. |
| 7,575,566 B2 | 8/2009 | Scheib |
| 7,591,813 B2 | 9/2009 | Levine et al. |
| 7,615,067 B2 | 11/2009 | Lee et al. |
| 7,617,005 B2 | 11/2009 | Demarais et al. |
| 7,637,903 B2 | 12/2009 | Lentz et al. |
| 7,647,115 B2 | 1/2010 | Levin et al. |
| 7,647,124 B2 | 1/2010 | Williams |
| 7,653,438 B2 | 1/2010 | Deem et al. |
| 7,655,006 B2 | 2/2010 | Sauvageau et al. |
| 7,662,151 B2 | 2/2010 | Crompton, Jr. et al. |
| 7,674,411 B2 | 3/2010 | Berg et al. |
| 7,676,910 B2 | 3/2010 | Kiepen et al. |
| 7,682,319 B2 | 3/2010 | Martin et al. |
| 7,686,802 B2 | 3/2010 | Stevens-Wright |
| 7,695,451 B2 | 4/2010 | Bencini et al. |
| 7,699,843 B2 | 4/2010 | Sutter et al. |
| 7,702,397 B2 | 4/2010 | Fredricks et al. |
| 7,708,704 B2 | 5/2010 | Mitelberg et al. |
| 7,717,948 B2 | 5/2010 | Demarais et al. |
| 7,727,187 B2 | 6/2010 | Lentz |
| 7,729,782 B2 | 6/2010 | Williams et al. |
| 7,731,681 B2 | 6/2010 | Schaer et al. |
| 7,731,682 B2 | 6/2010 | Bencini et al. |
| 7,744,586 B2 | 6/2010 | Larson et al. |

(56) References Cited

U.S. PATENT DOCUMENTS

| | | | |
|---|---|---|---|
| 7,747,334 B2 | 6/2010 | Bly et al. |
| 7,758,564 B2 | 7/2010 | Long et al. |
| 7,766,868 B2 | 8/2010 | Goode et al. |
| 7,770,584 B2 | 8/2010 | Danek et al. |
| 7,771,410 B2 | 8/2010 | Venturelli |
| 7,771,421 B2 | 8/2010 | Stewart et al. |
| 7,780,646 B2 | 8/2010 | Farnholtz |
| 7,789,877 B2 | 9/2010 | Vanney |
| 7,792,589 B2 | 9/2010 | Levy, Jr. et al. |
| 7,806,872 B2 | 10/2010 | Ponzi |
| 7,815,637 B2 | 10/2010 | Ormsby et al. |
| 7,824,399 B2 | 11/2010 | Francischelli et al. |
| 7,833,191 B2 | 11/2010 | Flach et al. |
| 7,850,675 B2 | 12/2010 | Bell et al. |
| 7,850,685 B2 | 12/2010 | Kunis et al. |
| 7,854,740 B2 | 12/2010 | Carney |
| 7,867,219 B2 | 1/2011 | Chambers |
| 7,875,018 B2 | 1/2011 | Tockman et al. |
| 7,881,807 B2 | 2/2011 | Schaer |
| 7,890,188 B2 | 2/2011 | Zhang et al. |
| 7,892,233 B2 | 2/2011 | Hall et al. |
| 7,896,872 B2 | 3/2011 | Finch et al. |
| 7,905,828 B2 | 3/2011 | Brock et al. |
| 7,914,467 B2 | 3/2011 | Layman et al. |
| 7,938,828 B2 | 5/2011 | Koblish |
| 7,947,016 B2 | 5/2011 | Lentz |
| 7,955,298 B2 | 6/2011 | Carroll et al. |
| 7,955,326 B2 | 6/2011 | Paul et al. |
| 7,959,626 B2 | 6/2011 | Hong et al. |
| 7,959,630 B2 | 6/2011 | Taimisto et al. |
| 7,967,816 B2 | 6/2011 | Ocel et al. |
| 7,976,539 B2 | 7/2011 | Hlavka et al. |
| 7,985,215 B2 | 7/2011 | Guo et al. |
| 7,998,112 B2 | 8/2011 | Chow et al. |
| 8,019,435 B2 | 9/2011 | Hastings et al. |
| 8,034,050 B2 | 10/2011 | Sharareh et al. |
| 8,043,279 B2 | 10/2011 | Hisamatsu et al. |
| 8,062,284 B2 | 11/2011 | Booth |
| 8,100,859 B2 | 1/2012 | Patterson et al. |
| 8,123,739 B2 | 2/2012 | McQueen et al. |
| 8,131,371 B2 | 3/2012 | Demarais et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,428 B2 | 6/2012 | Truckai et al. |
| 8,257,351 B2 | 9/2012 | Stewart et al. |
| 8,337,492 B2 | 12/2012 | Kunis et al. |
| 8,347,891 B2 | 1/2013 | Demarais et al. |
| 8,380,275 B2 | 2/2013 | Kim et al. |
| 8,454,594 B2 | 6/2013 | Demarais et al. |
| 8,548,600 B2 | 10/2013 | Deem et al. |
| 8,571,665 B2 | 10/2013 | Moffitt |
| 2001/0005785 A1 | 6/2001 | Sachse |
| 2001/0007070 A1 | 7/2001 | Stewart et al. |
| 2001/0020174 A1 | 9/2001 | Koblish |
| 2001/0031971 A1 | 10/2001 | Dretler et al. |
| 2001/0044596 A1 | 11/2001 | Jaafar |
| 2002/0002329 A1 | 1/2002 | Avitall |
| 2002/0004631 A1 | 1/2002 | Jenkins et al. |
| 2002/0004644 A1 | 1/2002 | Koblish |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0062124 A1 | 5/2002 | Keane |
| 2002/0065541 A1 | 5/2002 | Fredricks et al. |
| 2002/0072782 A1 | 6/2002 | Osorio et al. |
| 2002/0087208 A1 | 7/2002 | Koblish et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050637 A1 | 3/2003 | Maguire et al. |
| 2003/0050681 A1 | 3/2003 | Pianca |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0088244 A1 | 5/2003 | Swanson et al. |
| 2003/0100924 A1 | 5/2003 | Foreman et al. |
| 2003/0120270 A1 | 6/2003 | Acker |
| 2003/0125790 A1 | 7/2003 | Fastovsky |
| 2003/0144658 A1 | 7/2003 | Schwartz et al. |
| 2003/0150464 A1 | 8/2003 | Casscells |
| 2003/0153967 A1 | 8/2003 | Koblish et al. |
| 2003/0158584 A1 | 8/2003 | Cates et al. |
| 2003/0181897 A1 | 9/2003 | Thomas et al. |
| 2003/0181963 A1 * | 9/2003 | Pellegrino et al. ............... 607/96 |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0204187 A1 | 10/2003 | Hintringer |
| 2003/0216721 A1 | 11/2003 | Diederich et al. |
| 2003/0216792 A1 * | 11/2003 | Levin et al. .................... 607/48 |
| 2003/0220521 A1 | 11/2003 | Reitz et al. |
| 2003/0225331 A1 | 12/2003 | Diederich et al. |
| 2003/0229340 A1 | 12/2003 | Sherry et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0015193 A1 * | 1/2004 | Lamson et al. ................... 607/9 |
| 2004/0019364 A1 | 1/2004 | Kieval et al. |
| 2004/0019371 A1 | 1/2004 | Jaafar et al. |
| 2004/0024392 A1 | 2/2004 | Lewis et al. |
| 2004/0030375 A1 | 2/2004 | Pierce |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193149 A1 | 9/2004 | Koblish |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010095 A1 | 1/2005 | Stewart et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |

(56) References Cited

U.S. PATENT DOCUMENTS

| | | |
|---|---|---|
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096647 A1 | 5/2005 | Steinke et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004346 A1 | 1/2006 | Begg |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074403 A1 | 4/2006 | Rafiee |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0095030 A1 | 5/2006 | Avitall et al. |
| 2006/0100618 A1 | 5/2006 | Chan et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135870 A1 | 6/2006 | Webler |
| 2006/0135953 A1 | 6/2006 | Kania et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0182873 A1 | 8/2006 | Klisch et al. |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0241366 A1 | 10/2006 | Falwell et al. |
| 2006/0253115 A1 | 11/2006 | Avitall et al. |
| 2006/0253116 A1 | 11/2006 | Avitall et al. |
| 2006/0265014 A1 | 11/2006 | Demarais et al. |
| 2006/0265015 A1 | 11/2006 | Demarais et al. |
| 2007/0066972 A1 | 3/2007 | Ormsby et al. |
| 2007/0083194 A1 | 4/2007 | Kunis et al. |
| 2007/0142864 A1 | 6/2007 | Libbus et al. |
| 2007/0156200 A1 | 7/2007 | Kornet et al. |
| 2007/0208382 A1 | 9/2007 | Yun |
| 2007/0265687 A1 | 11/2007 | Deem et al. |
| 2007/0270791 A1 | 11/2007 | Wang et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0045921 A1 | 2/2008 | Anderson et al. |
| 2008/0091255 A1 | 4/2008 | Caparso et al. |
| 2008/0097398 A1 | 4/2008 | Mitelberg et al. |
| 2008/0108975 A1 | 5/2008 | Appling et al. |
| 2008/0109011 A1 | 5/2008 | Thenuwara et al. |
| 2008/0140150 A1 | 6/2008 | Zhou et al. |
| 2008/0213331 A1 | 9/2008 | Gelfand et al. |
| 2008/0249525 A1 | 10/2008 | Lee et al. |
| 2008/0255539 A1 | 10/2008 | Booth |
| 2008/0255642 A1 | 10/2008 | Zarins et al. |
| 2008/0288039 A1 | 11/2008 | Reddy |
| 2008/0300587 A1 | 12/2008 | Anderson |
| 2008/0319513 A1 | 12/2008 | Pu et al. |
| 2009/0018534 A1 | 1/2009 | Taimisto et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0204060 A1 | 8/2009 | Desinger et al. |
| 2009/0209943 A1 | 8/2009 | Marsman |
| 2009/0287202 A1 | 11/2009 | Ingle et al. |
| 2009/0306650 A1 | 12/2009 | Govari et al. |
| 2009/0306651 A1 | 12/2009 | Schneider |
| 2009/0312606 A1 | 12/2009 | Dayton et al. |
| 2010/0004632 A1 | 1/2010 | Wu et al. |
| 2010/0010567 A1 | 1/2010 | Deem et al. |
| 2010/0022989 A1 | 1/2010 | Parasmo et al. |
| 2010/0030112 A1 | 2/2010 | Anderson et al. |
| 2010/0057037 A1 | 3/2010 | Webler |
| 2010/0057150 A1 | 3/2010 | Demarais et al. |
| 2010/0069882 A1 | 3/2010 | Jennings et al. |
| 2010/0094281 A1 | 4/2010 | Hauck et al. |
| 2010/0099952 A1 | 4/2010 | Adams |
| 2010/0100073 A1 | 4/2010 | Lentz et al. |
| 2010/0137860 A1 | 6/2010 | Demarais et al. |
| 2010/0137952 A1 | 6/2010 | Demarais et al. |
| 2010/0168666 A1 | 7/2010 | Tegg |
| 2010/0168731 A1 | 7/2010 | Wu et al. |
| 2010/0168739 A1 | 7/2010 | Wu et al. |
| 2010/0168777 A1 | 7/2010 | Stangenes et al. |
| 2010/0174282 A1 | 7/2010 | Demarais et al. |
| 2010/0179512 A1 | 7/2010 | Chong et al. |
| 2010/0191112 A1 | 7/2010 | Demarais et al. |
| 2010/0204692 A1 | 8/2010 | Stewart et al. |
| 2010/0217184 A1 | 8/2010 | Koblish et al. |
| 2010/0217261 A1 | 8/2010 | Watson |
| 2010/0222851 A1 | 9/2010 | Deem et al. |
| 2010/0222854 A1 | 9/2010 | Demarais et al. |
| 2010/0228112 A1 | 9/2010 | Von Malmborg |
| 2010/0228152 A1 | 9/2010 | Fisher et al. |
| 2010/0249773 A1 | 9/2010 | Clark et al. |
| 2010/0261990 A1 | 10/2010 | Gillis et al. |
| 2010/0268307 A1 | 10/2010 | Demarais et al. |
| 2010/0280316 A1 | 11/2010 | Dietz et al. |
| 2010/0318081 A1 | 12/2010 | Sato et al. |
| 2010/0324482 A1 | 12/2010 | Farnholtz |
| 2010/0331776 A1 | 12/2010 | Salahieh et al. |
| 2011/0034989 A1 | 2/2011 | Al-Marashi et al. |
| 2011/0040238 A1 | 2/2011 | Wulfman et al. |
| 2011/0046607 A1 | 2/2011 | Halevy |
| 2011/0054464 A1 | 3/2011 | Werneth et al. |
| 2011/0060314 A1 | 3/2011 | Wallace et al. |
| 2011/0066105 A1 | 3/2011 | Hart et al. |
| 2011/0118582 A1 | 5/2011 | De la Rama et al. |
| 2011/0137298 A1 | 6/2011 | Nguyen et al. |

(56) References Cited

U.S. PATENT DOCUMENTS

| | | | |
|---|---|---|---|
| 2011/0144639 A1 | 6/2011 | Govari | |
| 2011/0160719 A1 | 6/2011 | Govari et al. | |
| 2011/0178505 A1 | 7/2011 | Odland et al. | |
| 2011/0245808 A1 | 10/2011 | Voeller et al. | |
| 2011/0257564 A1 | 10/2011 | Demarais et al. | |
| 2011/0264086 A1 | 10/2011 | Ingle | |
| 2011/0276034 A1 | 11/2011 | Tomarelli et al. | |
| 2011/0306851 A1 | 12/2011 | Wang | |
| 2011/0319908 A1 | 12/2011 | Thenuwara et al. | |
| 2012/0010607 A1 | 1/2012 | Malecki et al. | |
| 2012/0029505 A1 | 2/2012 | Jenson | |
| 2012/0029509 A1 | 2/2012 | Smith | |
| 2012/0029510 A1 | 2/2012 | Haverkost | |
| 2012/0029512 A1 | 2/2012 | Willard et al. | |
| 2012/0029513 A1 | 2/2012 | Smith et al. | |
| 2012/0035615 A1 | 2/2012 | Koester et al. | |
| 2012/0078076 A1 | 3/2012 | Stewart et al. | |
| 2012/0101553 A1 | 4/2012 | Reddy | |
| 2012/0116382 A1 | 5/2012 | Ku et al. | |
| 2012/0116383 A1 | 5/2012 | Mauch et al. | |
| 2012/0123258 A1 | 5/2012 | Willard | |
| 2012/0123406 A1 | 5/2012 | Edmunds et al. | |
| 2012/0130368 A1 | 5/2012 | Jenson | |
| 2012/0143097 A1 | 6/2012 | Pike, Jr. | |
| 2012/0143293 A1 | 6/2012 | Mauch et al. | |
| 2012/0157992 A1 | 6/2012 | Smith et al. | |
| 2012/0184952 A1 | 7/2012 | Jenson et al. | |
| 2012/0191083 A1 | 7/2012 | Moll et al. | |
| 2012/0197246 A1 | 8/2012 | Mauch | |
| 2012/0245577 A1 | 9/2012 | Mihalik et al. | |
| 2012/0265198 A1 | 10/2012 | Crow et al. | |
| 2012/0277842 A1 | 11/2012 | Kunis | |
| 2012/0290053 A1 | 11/2012 | Zhang et al. | |
| 2012/0310065 A1 | 12/2012 | Falwell et al. | |
| 2012/0310239 A1 | 12/2012 | Stewart et al. | |
| 2012/0323233 A1 | 12/2012 | Maguire et al. | |
| 2013/0012866 A1 | 1/2013 | Deem et al. | |
| 2013/0035681 A1 | 2/2013 | Subramaniam et al. | |
| 2013/0053876 A1 | 2/2013 | Ogle | |
| 2013/0090637 A1 | 4/2013 | Sliwa | |
| 2013/0090647 A1 | 4/2013 | Smith | |
| 2013/0090649 A1 | 4/2013 | Smith et al. | |
| 2013/0096553 A1 | 4/2013 | Hill et al. | |
| 2013/0116685 A1 | 5/2013 | Deem et al. | |
| 2013/0131667 A1 | 5/2013 | Jenson et al. | |
| 2013/0165921 A1 | 6/2013 | Sutermeister et al. | |
| 2013/0172872 A1 | 7/2013 | Subramaniam et al. | |
| 2013/0172879 A1 | 7/2013 | Sutermeister et al. | |
| 2013/0172880 A1 | 7/2013 | Willard | |
| 2013/0184773 A1 | 7/2013 | Libbus | |
| 2013/0253628 A1 | 9/2013 | Chaska | |
| 2013/0274614 A1 | 10/2013 | Shimada | |
| 2013/0274730 A1 | 10/2013 | Anderson | |
| 2013/0274731 A1 | 10/2013 | Anderson | |
| 2013/0274737 A1 | 10/2013 | Wang | |
| 2013/0282000 A1 | 10/2013 | Parsonage | |
| 2013/0282084 A1 | 10/2013 | Mathur | |
| 2013/0289686 A1 | 10/2013 | Masson | |
| 2013/0304047 A1 | 11/2013 | Grunewald | |
| 2013/0304052 A1 | 11/2013 | Rizq et al. | |
| 2013/0304062 A1 | 11/2013 | Chan | |
| 2014/0058376 A1 | 2/2014 | Horn | |

FOREIGN PATENT DOCUMENTS

| | | |
|---|---|---|
| CN | 102198015 | 9/2011 |
| CN | 102266245 | 12/2011 |
| CN | 102274075 | 12/2011 |
| CN | 102488552 | 6/2012 |
| CN | 102551874 | 7/2012 |
| CN | 102551878 A | 7/2012 |
| CN | 102631240 | 8/2012 |
| CN | 202386778 | 8/2012 |
| CN | 102688093 | 9/2012 |
| CN | 202426649 | 9/2012 |
| CN | 102743225 | 10/2012 |
| CN | 202537649 | 11/2012 |
| CN | 202538132 | 11/2012 |
| CN | 102885648 | 1/2013 |
| CN | 102885649 | 1/2013 |
| CN | 102908188 | 2/2013 |
| CN | 102908189 | 2/2013 |
| CN | 202761434 | 3/2013 |
| CN | 202843784 | 4/2013 |
| DE | 3151180 A1 | 8/1982 |
| DE | 29909082 | 7/1999 |
| DE | 10252325 | 5/2004 |
| DE | 10257146 | 6/2004 |
| DE | 20 2004 021 941 | 5/2013 |
| DE | 20 2004 021 942 | 5/2013 |
| DE | 20 2004 021 949 | 5/2013 |
| DE | 20 2004 021 951 | 6/2013 |
| DE | 20 2004 021 952 | 6/2013 |
| DE | 20 2004 021 953 | 6/2013 |
| DE | 20 2004 021 944 | 7/2013 |
| EP | 0132344 | 1/1985 |
| EP | 0132344 | 1/1986 |
| EP | 0510624 | 10/1992 |
| EP | 0348136 B1 | 8/1993 |
| EP | 510624 | 7/1995 |
| EP | 732080 | 9/1996 |
| EP | 0779079 | 6/1997 |
| EP | 0811395 A2 | 6/1997 |
| EP | 0821602 | 2/1998 |
| EP | 0868923 | 10/1998 |
| EP | 0728495 | 4/1999 |
| EP | 0521595 B1 | 5/1999 |
| EP | 0916360 | 5/1999 |
| EP | 0937481 A1 | 8/1999 |
| EP | 1042990 | 10/2000 |
| EP | 1233716 | 8/2002 |
| EP | 963191 | 8/2003 |
| EP | 757575 | 9/2003 |
| EP | 873760 | 1/2004 |
| EP | 779079 | 3/2004 |
| EP | 0951244 B1 | 3/2004 |
| EP | 0778043 | 11/2005 |
| EP | 1042990 | 10/2006 |
| EP | 1733689 | 12/2006 |
| EP | 1802370 | 7/2007 |
| EP | 1009303 | 6/2009 |
| EP | 2092957 | 8/2009 |
| EP | 2106821 | 10/2009 |
| EP | 1982741 B1 | 6/2010 |
| EP | 2208474 | 7/2010 |
| EP | 2263588 | 12/2010 |
| EP | 2332607 | 6/2011 |
| EP | 2519173 | 11/2012 |
| EP | 2558016 | 2/2013 |
| EP | 2598069 | 6/2013 |
| EP | 2664295 | 11/2013 |
| JP | 355137141 | 10/1980 |
| WO | WO-85/01213 | 3/1985 |
| WO | WO-91/04725 | 4/1991 |
| WO | WO-9115254 | 10/1991 |
| WO | WO-9211898 | 7/1992 |
| WO | WO-9220291 | 11/1992 |
| WO | WO-93/02740 | 2/1993 |
| WO | WO-93/07803 | 4/1993 |
| WO | WO-94/00188 | 1/1994 |
| WO | WO/94/11057 | 5/1994 |
| WO | WO-9421168 | 9/1994 |
| WO | WO-9510319 | 4/1995 |
| WO | WO-9513111 | 5/1995 |
| WO | WO-9520416 | 8/1995 |
| WO | WO/95/25472 | 9/1995 |
| WO | WO-9531142 | 11/1995 |
| WO | WO-95/33514 | 12/1995 |
| WO | WO/96/00039 | 1/1996 |
| WO | WO-9600036 | 1/1996 |
| WO | WO-96/04957 | 2/1996 |
| WO | WO-96/11723 | 4/1996 |
| WO | WO-9632980 | 10/1996 |

(56) References Cited

FOREIGN PATENT DOCUMENTS

| | | |
|---|---|---|
| WO | WO-9634559 | 11/1996 |
| WO | WO-9638196 | 12/1996 |
| WO | WO/97/13463 | 4/1997 |
| WO | WO-97/13550 | 4/1997 |
| WO | WO-9717892 | 5/1997 |
| WO | WO-9736548 | 10/1997 |
| WO | WO-97/49453 | 12/1997 |
| WO | WO-9802201 | 1/1998 |
| WO | WO-9833469 | 8/1998 |
| WO | WO-98/37926 | 9/1998 |
| WO | WO/98/42403 | 10/1998 |
| WO | WO-98/43700 | 10/1998 |
| WO | WO-98/43701 | 10/1998 |
| WO | WO-9843530 | 10/1998 |
| WO | WO-98/48888 | 11/1998 |
| WO | WO-99/00060 | 1/1999 |
| WO | WO-9911313 A1 | 3/1999 |
| WO | WO-99/33407 | 7/1999 |
| WO | WO-99/51286 | 10/1999 |
| WO | WO-99/52424 | 10/1999 |
| WO | WO-9952424 | 10/1999 |
| WO | WO-9956801 | 11/1999 |
| WO | WO-9962413 | 12/1999 |
| WO | WO 0001313 | 1/2000 |
| WO | WO-0056237 | 9/2000 |
| WO | WO-0067832 | 11/2000 |
| WO | WO-01/26729 | 4/2001 |
| WO | WO-0122897 | 4/2001 |
| WO | WO-0137723 | 5/2001 |
| WO | WO-0137746 | 5/2001 |
| WO | WO0170114 | 9/2001 |
| WO | WO-0170114 | 9/2001 |
| WO | WO-0180758 | 11/2001 |
| WO | WO-0208301 | 1/2002 |
| WO | WO-02/09808 | 2/2002 |
| WO | WO-02/26314 | 4/2002 |
| WO | WO-0245608 | 6/2002 |
| WO | WO-02/053207 | 7/2002 |
| WO | WO-02/070039 A2 | 9/2002 |
| WO | WO-02/070047 | 9/2002 |
| WO | WO-02/085448 | 10/2002 |
| WO | WO-02083017 | 10/2002 |
| WO | WO/02085192 | 10/2002 |
| WO | WO-02087453 | 11/2002 |
| WO | WO-02089687 | 11/2002 |
| WO | WO-02089908 | 11/2002 |
| WO | WO-03/018108 | 3/2003 |
| WO | WO-03020334 | 3/2003 |
| WO | WO-03/028802 | 4/2003 |
| WO | WO-03/063692 | 8/2003 |
| WO | WO-03/071140 A2 | 8/2003 |
| WO | WO-03/076008 | 9/2003 |
| WO | WO-03/082080 | 10/2003 |
| WO | WO-03/082403 | 10/2003 |
| WO | WO-03082080 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004100813 | 11/2004 |
| WO | WO-2004/107965 | 12/2004 |
| WO | WO-2005014100 | 2/2005 |
| WO | WO-2005016165 | 2/2005 |
| WO | WO 2005/032646 | 4/2005 |
| WO | WO/2005/032646 | 4/2005 |
| WO | WO-2005037070 | 4/2005 |
| WO | WO-2005041748 | 5/2005 |
| WO | WO-2005051216 | 6/2005 |
| WO | WO-2005/065284 | 7/2005 |
| WO | WO-2005070491 | 8/2005 |
| WO | WO-2005/084389 A2 | 9/2005 |
| WO | WO-2005/097256 A2 | 10/2005 |
| WO | WO-2005/110528 | 11/2005 |
| WO | WO/2005/110528 | 11/2005 |
| WO | WO-2005/123183 | 12/2005 |
| WO | WO-2006/007048 A2 | 1/2006 |
| WO | WO-2006018528 A1 | 2/2006 |
| WO | WO-2006020920 | 2/2006 |
| WO | WO-2006/031899 A2 | 3/2006 |
| WO | WO-2006022790 A1 | 3/2006 |
| WO | WO-2006041847 | 4/2006 |
| WO | WO-2006041881 | 4/2006 |
| WO | WO-2006065949 | 6/2006 |
| WO | WO-2006092000 | 9/2006 |
| WO | WO-2006105121 | 10/2006 |
| WO | WO-2007001981 | 1/2007 |
| WO | WO-2007008954 | 1/2007 |
| WO | WO-2007035537 | 3/2007 |
| WO | WO-2007078997 A2 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007128064 | 11/2007 |
| WO | WO-2007136979 | 11/2007 |
| WO | WO-2007146834 | 12/2007 |
| WO | WO-2008003058 | 1/2008 |
| WO | WO-2008061150 | 5/2008 |
| WO | WO-2008061152 | 5/2008 |
| WO | WO-2008070413 | 6/2008 |
| WO | WO-2008101244 | 8/2008 |
| WO | WO-2009121017 | 1/2009 |
| WO | WO-2009108997 A1 | 9/2009 |
| WO | WO-2009125575 A1 | 10/2009 |
| WO | WO-2010048676 | 5/2010 |
| WO | WO-2010078175 A1 | 7/2010 |
| WO | WO-2010091701 | 8/2010 |
| WO | WO-2010120835 | 10/2010 |
| WO | WO-2011015218 | 2/2011 |
| WO | WO-2011019838 | 2/2011 |
| WO | WO-2011082279 | 7/2011 |
| WO | WO-2011130534 | 10/2011 |
| WO | WO-2012075156 | 6/2012 |
| WO | WO-2012130337 | 10/2012 |
| WO | WO-2012131107 | 10/2012 |
| WO | WO-2012154219 | 11/2012 |
| WO | WO-2012154796 | 11/2012 |
| WO | WO-2013016203 | 1/2013 |
| WO | WO-2013028993 | 2/2013 |
| WO | WO-2013040201 | 3/2013 |
| WO | WO-2013049601 | 4/2013 |
| WO | WO-2013055537 | 4/2013 |
| WO | WO-2013058962 | 4/2013 |
| WO | WO-2013101452 | 7/2013 |
| WO | WO-2013106054 | 7/2013 |
| WO | WO2013109318 | 7/2013 |
| WO | WO2013158676 | 10/2013 |
| WO | WO2013158678 | 10/2013 |
| WO | WO2013165920 | 11/2013 |
| WO | WO2013154776 | 12/2013 |

OTHER PUBLICATIONS

U.S. Appl. No. 10/900,199, filed Jul. 28, 2004, Gelfand.
U.S. Appl. No. 11/129,765, filed May 13, 2005, Deem.
U.S. Appl. No. 11/133,925, filed May 20, 2005, Gelfand.
U.S. Appl. No. 11/144,173, filed Jun. 3, 2005, Levin et al.
U.S. Appl. No. 11/144,298, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.
U.S. Appl. No. 11/233,814, Denise Demarais.
U.S. Appl. No. 11/252,462, Denise Demarais.
U.S. Appl. No. 11/266,993, Demarais.
U.S. Appl. No. 11/324,188, Denise Demarais.
U.S. Appl. No. 11/368,577, Demarais.
U.S. Appl. No. 11/368,809, Denise Demarais.
U.S. Appl. No. 11/368,949, Denise Demarais.
U.S. Appl. No. 11/368,971, Denise Demarais.
U.S. Appl. No. 60/236,420, Harrison et al.
U.S. Appl. No. 60/370,190.
U.S. Appl. No. 60/408,665.
U.S. Appl. No. 60/415,575.

(56) References Cited

OTHER PUBLICATIONS

U.S. Appl. No. 60/442,970.
"2003 European Society of Hypertension-European Society of Cardiology guidelines for the management of arterial hypertension," Journal of Hypertension 2003, vol. 21, No. 6, pp. 1011-1053.
"Advanced Neuromodulation Systems' Comparison Chart," 1 page.
"Advances in the role of the sympathetic nervous system in cardiovascular medicine," 2001 SNS Report, No. 3, Springer, published with an educational grant from Servier, pp. 1-8.
"Atrial Fibrillation" Heart and Vascular Health on Yahoo! Health. 2 pages. <URL:http://health.yahoo.com/topic/heart/overview/article/healthwise/hw160872;_ylt=AiBT43Ey74HQ7ft3jAb4C.sPu7cF>.
"Cardiac Glycosides," Heart Disease—A Text Book of Cardiovascular Medicine vol. 2, Edited by Eugene Braunwald, 5th Edition, WB Saunders Company, pp. 480-481.
"Clinical Trials in Hypertension and Renal Diseases," Slide Source, www.hypertensiononline.org, 33 pages.
"ECM 830 Specifications Sheet," tech@genetronics.com, 20-001796-01 Rev D, 2 pages.
"Effects of Renal Failure on the Cardiovascular System," 5th Edition Heart Disease, A Textbook of Cardiovascular Medicine, vol. 2, Edited by Eugene Braunwald, W.B. Saunders Company, pp. 1923-1925.
"Electrical Stimulation for the Treatment of Chronic Wounds," Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pages.
"Electropermeabilization (Electroporation)," Cyto Pulse Sciences Inc., http://www.cytopulse.com/electroporation.html (last accessed Mar. 3, 2005), 3 pages.
"Electroporation based Technologies and Treatments," ESPE Newsletter No. 6, QLK 02002-2003, Jan. 2005, www.cliniporator.com, 4 pages.
"End-stage renal disease payment policies in traditional Medicare," Report to the Congress: Medicare Payment Policy, Mar. 2001, Medpac, pp. 123-138.
"Epidemiology of Renal Disease in Hypertension," slide presentation by hypertensiononline.org, 21 pages.
"Fact Book Fiscal Year 2003," National Institutes of Health National Heart, Lung, and Blood Institute, Feb. 2004, 197 pages.
"Heart Arrhythmia" Heart and Vascular Health on Yahoo! Health. 13 pages. <URL:http://health.yahoo.com/topic/heart/overview/article/mayoclinic/21BBE2B0-128D-4AA2-A5CE215065586678;_ylt=Aqd9M5rNyHD0sbPOmHXFhLcPu7cF>.
"Heart Disease and Stroke Statistics—2004 update," American Heart Association, American Stroke Association, Dallas, Texas, © 2003 American Heart Association, 52 pages.
"Hypertension and Renal Disease: Mechanisms," Slide Show by www.hypertensiononline.org, 22 pages.
"Hypertension Incidence and Prevalence, Age Specific Rates, by Gender, B.C., 2001/2002," Graph., Chronic Disease Management, May 2003, British Columbia Ministry of Health Services, 1 page.
Implantable Pump—The Medtronic MiniMed 2007 Implantable Insulin Pump System, Medtronic MiniMed 2004, 4 pages.
"Infumedics Inc.," Background and products paper and comparison of Medtronic SynchroMed II and Infumedics Prometra pumps, 3 pages.
"Introduction to Autonomic Pharmacology," Chapter 3, Part 2 Autonomic Pharmacology, pp. 18-26.
"Isovue: Data Sheet". Regional Health Limited. 8 pages. Mar. 11, 2003.
"Market for infusion pumps grows with an aging population," NWL 97-01, The BBI Newsletter, vol. 20, No. 2, Feb. 1, 1997, American Health Consultants Inc., 6 pages.
"Micro ETS Hyperhidrosis USA" Hyperhidrosis USA. 2 pages. <URL:http://www.hyperhidrosis-usa.com/Index.html>.

"PHCL 762 Pharmacology of the Autonomic Nervous System," Chapter 2 and 6.8 in Mosby, http://www.kumc.edu/research/medicine/pharmacology/CAI/phcl762.html, last accessed Aug. 24, 2004, 14 pages.
"Programmable Infusion System," Pumps and Pump Selection, Medtronic Pain Therapies, Medtronic, Inc. Sep. 5, 2001, 2 pages.
"Pulmonary Concepts in Critical Care Breath Sounds," http://rnbob.tripod.com/breath.htm, last accessed Aug. 23, 2004, 5 pages.
"Pulmonary Function Testing," http://jan.ucc.nau.edu/~daa/lecture/pft.htm, last accessed Aug. 23, 2004, 8 pages.
"Renal Parenchymal Disease," Ch. 26, 5th Edition Heart Disease, A Textbook of Cardiovascular Medicine vol. 2, Edited by Eugene Braunwald, WB Saunders Company, pp. 824-825.
"Sensorcaine-MPF Spinal Injection," informational document, AstraZeneca 2001, 2 pages.
"Summary," Critical Reviews in Biomedical Engineering, vol. 17, Issue 5, 1989, pp. 515-529.
"The Antihypertensive and Lipid-Lowering Treatment to Prevent Heart Attack Trial," ALLHAT Research Group, JAMA 2002, vol. 288, pp. 2981-2997.
Aars, H. And S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.
Abramov, G.S. et al., "Alteration in sensory nerve function following electrical shock," Burns vol. 22, No. 8, © 1996 Elsevier Science Ltd., pp. 602-606.
Achar, Suraj, M.D. And Suriti Kundu, M.D., "Principles of Office Anesthesia: Part I. Infiltrative Anesthesia," Office Procedures, American Family Physician, Jul. 1, 2002, vol. 66, No. 1, pp. 91-94.
Agnew, William F. et al., "Evolution and Resolution of Stimulation-Induced Axonal Injury in Peripheral Nerve," May 21, 1999, Muscle and Nerve, vol. 22, Oct. 1999, © 1999 John Wiley & Sons, pp. 1393-1402.
Ahadian, Farshad M., M.D., "Pulsed Radiofrequency Neurotomy: Advances in Pain Medicine," Current Pain and Headache Reports 2004, vol. 8, © 2004 Current Science Inc., pp. 34-40.
Alford, J.Winslow, M.D. And Paul. D. Fadale, M.D., "Evaluation of Postoperative Bupivacaine Infusion for Pain Management After Anterior Cruciate Ligament Reconstruction," The Journal of Arthroscopic and Related Surgery Oct., vol. 19, No. 8, © 2003 Arthroscopy Association of North America, pp. 855-861.
Amersham Health. "Hypaque-Cysto" 6 pages. 2003.
Andrews, B.T. et al., "The use of surgical sympathectomy in the treatment of chronic renal pain," Mar. 5, 1997, British Journal of Urology, vol. 80, © 1997 British Journal of Urology, pp. 6-10.
Antman, Elliott M. And Eugene Braunwald, "Chapter 37—Acute Myocardial Infarction," Heart Disease—A Textbook of Cardiovascular Medicine, 5th Edition, vol. 2, 1997, Edited by Eugene Braunwald, pp. 1184-1288.
Archer, Steffan et al., "Cell Reactions to Dielectrophoretic Manipulation," Mar. 1, 1999, Biochemical and Biophysical Research Communications, 1999 Academic Press, pp. 687-698.
Arentz, Thomas et al. "Incidence of pulmonary vein stenosis 2 years after radiofrequency catheter ablation of refractory atrial fibrillation." European Heart Journal. 2003. 24; pp. 963-969.
Arias, Manuel J., M.D., "Percutaneous Radio Frequency Thermocoagulation with Low Temperature in the Treatment of Essential Glossopharyngeal Neuralgia," Surg. Neurol. 1986, vol. 25, © 1986 Elsevier Science Publishing Co. Inc., pp. 94-96.
Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.
Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.
Augustyniak, Robert A. et al., "Sympathetic Overactivity as a Cause of Hypertension in Chronic Renal Failure," Aug. 14, 2001, Journal of Hypertension, 2002, vol. 20, 2002 Lippincott Williams & Wilkins, pp. 3-9.

(56) References Cited

OTHER PUBLICATIONS

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg, 1991, vol. 72, © 1991 The International Anesthesia Research Society, pp. 773-778.

Balazs, Tibor, "Development of Tissue Resistance to Toxic Effects of Chemicals," Jan. 26, 1974, Toxicology, vol. 2, © 1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © 2001 the American Physiological Society, pp. R1534-R1545.

Barrett, Carolyn J. et al., "What Sets the Long-Term Level of Renal Sympathetic Nerve Activity?," May 12, 2003, Integrative Physiology, Circulation Research 2003, vol. 92, © 2003 American Heart Association, pp. 1330-1336.

Bassett, C. Andrew L. et al., "Augmentation of Bone Reapair by Inductively Coupled Electromagnetic Fields," May 3, 1974, Science, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, 2004, © 2004 IOP Publishing Ltd., pp. 1077-1093.

Berde, Charles and Gary R. Strichartz, "Local Anesthetics," Anesthesia, Chapter 13, 5th addition, Churchill-Livingston, Philadelphia 2000, pp. 491-521.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 3, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Bigler, D. et al., "Tachyphylaxis during postoperative epidural analgesia—new insights," Apr. 15, 1987, Letter to the Editor, Acta Anesthesiol. Scand. 1987, vol. 31, pp. 664-665.

Binder, Allan et al., "Pulsed Electromagnetic Field Therapy of Persistent Rotator Cuff Tendinitis," The Lancet, Saturday Mar. 31, 1984, The Lancet Ltd., pp. 695-698.

Black, Henry R., M.D., "Resistant Hypertension 2004," presentation at Rush University Medical Center, Jul. 15, 2004, 40 pages.

Blad, B., et al., "An Electrical Impedance index to Assess Electroporation in Tissue," Tissue and Organ (Therapy) 2001, Oslo, pp. 31-34.

Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.

Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Bourge, Robert C. "Heart Failure Monitoring Devices: Rationale and Status" 28 pages.

Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.

Bunch, Jared T. et al. "Mechanisms of Phrenic Nerve Injury During Radiofrequency Ablation at the Pulmonary Vein Orifice." Journal of Cardiovascular Electrophysiology. vol. 16, No. 12. pp. 1318-1325. Dec. 2005.

Burkhoff, Daniel. "Interventional Device-Based Therapy for CHF Will Redefine Current Treatment Paradigms". Columbia University. 2004. 32 slides.

Cahana, A. et al., "Acute Differential Modulation of Synaptic Transmission and Cell Survival During Exposure to Pulsed and Continuous Radiofrequency Energy," The Journal of Pain, May 2003, vol. 4, No. 4, © 2003 by the American Pain Society, pp. 197-202.

Cahana, Alex, M.D., "Pulsed Radiofrequency: A Neurobiologic and Clinical Reality," May 17, 2005, Anesthesiology 2005, vol. 103, No. 6, Dec. 2005, © 2005 American Society of Anesthesiologists, Inc., Lippincott Williams & Wilkins, Inc., p. 1311.

Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Campese, V.M. et al., "Renal Afferent Denervation Prevents the Progression of Renal Disease in the Renal Ablation Model of Chronic Renal Failure in the Rat," Jun. 13, 1995, American Journal of Kidney Diseases 1995, vol. 26, No. 5, 1995 the National Kidney Foundation, Inc., pp. 861-865.

Campese, V.M., "A new model of neurogenic hypertension caused by renal injury: pathophysiology and therapeutic implications," Clin. Exp. Nephrol 2003, vol. 7, © 2003 Japanese Society of Nephroloogy, pp. 167-171.

Campese, V.M., "Neurogenic factors and hypertension in chronic renal failure," Journal of Nephrology, vol. 10, No. 4, © 1997 Societa Italiana di Nefrologia, pp. 184-187.

Canbaz, Suat et al. "Electrophysiological evaluation of phrenic nerve injury during cardiac surgery—a prospective, controlled clinical study." BioMed Central. 5 pages. 2004.

Carls, G., et al., "Electrical and magnetic stimulation of the intercostal nerves: a comparative study," Electromyogr. clin. Neurophysiol., vol. 37, 1997, pp. 509-512.

Carlson, Scott H. And J. Michael Wyss, "e-Hyertension, Opening New Vistas," Introductory Commentary, Hypertension 2000, vol. 35, American Heart Association, Inc., 2000, p. 538.

Carson, Peter. "Device-based Treatment for Chronic Heart Failure: Electrical Modulation of Myocardial Contractility". Transcatheter Cardiovascular Therapeutics 2005. 21 slides.

Chang, Donald C., "Cell poration and cell fusion using an oscillating electric field," Biophysical Journal, vol. 56, Oct. 1989, Biophysical Society, pp. 641-652.

Chiou, CW et al. "Efferent Vagal Innervation of the Canine Atria and Sinus and Atrioventricular Nodes". Circulation. Jun. 1997. 95(11):2573-2584. Abstract only. 2 pages.

Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.

Codman 3000, Implantable Constant-Flow Infusion Pump Pamphlet, for Continuous Intrathecal Drug Delivery, 2 pages.

Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.

Converse Jr., R.L. et al., "Sympathetic Overactivity in Patients with Chronic Renal Failure," New England Journal of Medicine, Dec. 31, 1992, vol. 327 (27), pp. 1912-1918.

Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.

(56) References Cited

OTHER PUBLICATIONS

Cosman, Eric R., Ph.D., "A Comment on the History of the Pulsed Radiofrequency Technique for Pain Therapy," Anesthesiology Dec. 2005, vol. 103, No. 6, © 2005 American Society of Anesthesiologists, Inc. Lippincott Williams & Wilkins, Inc., p. 1312.

Crawford, William H. et al., "Pulsed Radio Frequency Therapy of Experimentally Induced Arthritis in Ponies," Dec. 18, 1989, Can. J. Vet. Res. 1991, vol. 55, pp. 76-85.

Cryovascular Systems, Inc. "Pre-Clinical Testing Establishing Parameters". PowerPoint Presentation. 18 slides.

Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.

Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, © 1998 International Neuromodulation Society, pp. 111-128.

Dang, Nicholas C. et al., "A Novel Approach to Increase Total Urine Output in Heart Failure: Renal Nerve Blockade," ACC 2005 poster, 1 page.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Davalos, R. et al., "Electrical Impedance Tomography for Imaging Tissue Electroporation," Jul. 25, 2003, IEEE Transactions on Biomedical Engineering, vol. 51, No. 5, May 2004, IEEE 2004, pp. 761-767.

Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.

Deng, Jingdong et al., "The Effects of Intense Submicrosecond Electrical Pulses on Cells," Nov. 26, 2002, Biophysical Journal, vol. 84, Apr. 2003, © 2003 Biophysical Society, pp. 2709-2714.

Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.

Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.

Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.

DiBona, G., "Neural Control of the Kidney: Functionally Specific Renal Sympathetic Nerve Fibers," Starling Lecture, Am J Physiol Regulatory Integrative Comp Physiol 2000, 279, 2000 The American Physiological Society, pp. R1517-R1524.

Dibona, Gerald F., "Sympathetic Nervous System and the Kidney in Hypertension," Current Opinion in Nephrology and Hypertension 2002, vol. 11, 2002 Lippincott Williams & Wilkins, pp. 197-200.

Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R298-R305.

Dibona, Gerald F. and Ulla C. Kopp, "Neural Control of Renal Function," Physiological Reviews Jan. 1997, vol. 77, No. 1, © 1997 American Physiological Society, pp. 75-197.

Dibona, Gerald F. and Ulla C. Kopp, "Role of the Renal Sympathetic Nerves in Pathophysiological States," Neural Control of Renal Function, vol. 77, pp. 142-197.

Dibona, Gerald F., "Functionally Specific Renal Sympathetic Nerve Fibers: Role in Cardiovascular Regulation," Mar. 6, 2001, American Journal of Hypertension 2001, vol. 14, 2001 American Journal of Hypertension, Ltd. Published by Elsevier Science Inc., pp. 163S-170S.

Dibona, Gerald F., "Nervous Kidney—Interaction Between Renal Sympathetic Nerves and the Renin-Angiotensin System in the Control of Renal Function," Jun. 21, 2000, Hypertension 2000, vol. 36, 2000 American Heart Association, Inc., pp. 1083-1088.

Dibona, Gerald F., "Neural Control of the Kidney—Past, Present, and Future," Nov. 4, 2002, Novartis Lecture, Hypertension 2003, vol. 41, part 2, © 2002 American Heart Association, pp. 621-624.

Dibona, Gerald F., "Peripheral and Central Interactions between the Renin-Angiotensin System and the Renal Sympathetic Nerves in Control of Renal Function," Annals New York Academy of Sciences, pp. 395-406.

Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.

Dibona, Gerald F., "The Sympathetic Nervous System and Hypertension," Dec. 4, 2003, Hypertension Highlights, Hypertension Feb. 2004, vol. 43, © 2004 American Heart Association, pp. 147-150.

Dibona, Gerald F., L.L. Sawin, "Effect of renal denervation on dynamic autoregulation of renal blood flow," Feb. 12, 2004, Am J Physiol Renal Physiol 286, pp. F1209-F1218.

Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16, No. 8, Aug. 2005. pp. 845-852.

Dorros, Gerald, M.D., "Renal Artery Stenting State of the Art," presentation, TCT, Washington D.C., Sep. 2003, 27 pages.

Dueck, Ron, M.D., "Noninvasive Cardiac Output Monitoring," The Cardiopulmonary and Critical Care Journal, Chest, vol. 120, sec. 2, Aug. 2001, American College of Chest Physicians 2005, pp. 339-341, 5 pages.

Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.

Durand, D.M., "Electrical Field Effects in Hyperexcitable Neural Tissue: A Review," Radiation Protection Dosimetry, vol. 106, No. 4, 2003, Nuclear Technology Publishing, pp. 325-331.

Erdine, Serap and Alev Arat-Ozkan, "Resistant Hypertension," European Society of Hypertension Scientific Newsletter: Update on Hypertension Management, 2003, vol. 4, No. 15, 2 pages.

Fareed, Jawad, Ph.D. et al., "Some Objective Considerations for the Use of Heparins and Recombinant Hirudin in Percutaneous Transluminal Coronary Angioplasty," Seminars in Thrombosis and Hemostasis 1991, vol. 17, No. 4, © 1991 Thieme Medical Publishers, Inc., pp. 455-470.

Fava, M. "Clinical Testing Establishing Safety & Efficacy". PowerPoint Presentation. Cryovascular Systems, Inc. 14 slides.

Fava, M. et al. "Initial Human Experience with CryoPlasty™ in the Treatment of Infrainguinal Arterial Disease." Abstract. 1 page.

Ferguson, D.R. et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

Fernandez-Ortiz, Antonio et al., "A New Approach for Local Intravascular Drug Delivery—Iontophoretic Balloon," Intravascular Iontophoretic Local Delivery, Circulation, vol. 89, No. 4, Apr. 1994, pp. 1518-1522.

Fields, Larry E. et al, "The Burden of Adult Hypertension in the United States 1999 to 2000—A Rising Tide," May 18, 2004, © 2004 the American Heart Association, Hypertension Oct. 2004, pp. 1-7.

(56) References Cited

OTHER PUBLICATIONS

Fischell, Tim A. et al. "Ultrasonic Energy: Effects on Vascular Function and Integrity." Circulation: Journal of the American Heart Association. 1991. 84;pp. 1783-1795.
Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.
Fukuoka, Yuko et al., "Imaging of neural conduction block by neuromagnetic recording," Oct. 16, 2002, Clinical Neurophysiology 2002, vol. 113, © 2002 Elsevier Science Ireland Ltd., pp. 1985-1992.
Fuster, Valentin et al. "ACC/AHA/ESC Practice Guidelines: ACA/AHA/ESC 2006 Guidelines for the Management of Patients with Atrial Fibrillation." JACC vol. 48, No. 4, Aug. 15, 2006.
Gami, Apoor S., M.D. and Vesna D. Garovic, M.D., "Contrast Nephropathy After Coronary Angiography," Mayo Clin Proc. 2004, vol. 79, 2004 Mayo Foundation for Medical Education and Research, pp. 211-219.
Gattone II, Vincent H. et al., "Contribution of Renal Innervation to Hypertension in Polycystic Kidney Disease in the Rat," University of Chicago Section of Urology, 16 pages.
Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.
Gehl, Julie et al., "In vivo electroporation of skeletal muscle: threshold, efficacy and relation to electric field distribution," Biochimica et Biophysica Acta, 1428, 1999, Elsevier Science B.V. 1999, pp. 233-240.
Ghoname, El-sayed A. et al., "Percutaneous electrical nerve stimulation: an alternative to TENS in the management of sciatica," Apr. 26, 1999, Pain 1999, vol. 83, © 1999 International Association for the Study of Pain / Published by Elsevier Science B.V., pp. 193-199.
Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.
Goldberger, Jeffrey J. et al., "New technique for vagal nerve stimulation," Jun. 2, 1999, Journal of Neuroscience Methods 91, © 1999 Elsevier Science B.V., pp. 109-114.
Gorbunov, F.E. et al., "The Use of Pulsed and Continuous Short Wave Diathermy (Electric Field) in Medical Rehabilitation of the Patients with Guillain-Barre Syndrome and Other Peripheral Myelinopathies," May 6, 1994, 5 pagees (most of article in Russian language).
Greenwell, T.J. et al., "The outcome of renal denervation for managing loin pain haematuria syndrome," Oct. 30, 2003, Institute of Urology and Nephrology, London, UK, © 2004 BJU International, 4 pages.
Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, © 2000 by the American College of Cardiology, pp. 1542-1548.
Guimaraes, Sarfim. "Vascular Adrenoceptors: An Update" pp. 319-356.
Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.
Hammer, Leah W. "Differential Inhibition of Functional Dilation of Small Arterioles by Indomethacin and Glibenclamide." Hypertension. Feb. 2001 Part II. pp. 599-603.
Hamza, M.D., Mohamed A. et al., "Effect of the Duration of Electrical Stimulation on the Analgesic Response in Patients with Low Back Pain," Anesthesiology, vol. 91, No. 6, Dec. 1999, © 1999 American Society of Anesthesiologists, Inc., pp. 1622-1627.

Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.
Heida, Tjitske et al., "Investigating Membrane Breakdown of Neuronal Cells Exposed to Nonuniform Electric Fields by Finite-Element Modeling and Experiments," May 9, 2002. IEEE Transactions on Biomedical Engineering, vol. 49, No. 10, Oct. 2002, © 2002 IEEE, pp. 1195-1203.
Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.
Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, © 2001 Lippincott Williams & Wilkins Inc., pp. 239-244.
Hing, Esther, M.P.H. And Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.
Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.
Hopp, Francis A. and Jeanne L. Seagard, "Respiratory Responses to Selective Blockade of Carotid Sinus Baroreceptors in the Dog," Jun. 22, 2005, Am J Physiol Regul Integr Comp Physiol 1998, vol. 275, 2005 American Physiological Society, pp. R10-R18.
Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.
Horwich, Tamara, M.D., "New Advances in the Diagnosis and Management of Acute Decompensated Heart Failure," the Heart.org Satellite program, Rapid Review, CME Symposium presented on Nov. 8, 2004 at the Sheraton New Orleans Hotel, 4 pages.
Huang, Wann-Chu et al. "Renal Denervation Prevents and Reverses Hyperinsulinemia-Induced Hypertension in Rats," Mar. 25, 1998, Hypertension 1998, vol. 32, 1998 American Heart Association, Inc., pp. 249-254.
Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, © 2004 the American Physiological Society, pp. H2141-H2150.
Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.
International Search Report, PCT/US04/38498, Mailed Feb. 18, 2005, Applicant: G & L Consulting, LLC (3 pages).
Israili, Z.H., "Clinical pharmacokinetics of angiotensin II (AT) receptor blockers in hypertension," Journal of Human Hypertension 2000, Macmillan Publishers Ltd., vol. 14, pp. S73-S86.
Janda, J., "Impact of the electrical stimulation apparatus rebox on the course of ischemic renal damage in rats," British Library—"The world's knowledge" pp. 252-254 (translated and untranslated versions).
Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.
Jia, Jianping and Pollock, Martin. "The pathogenesis of non-freezing cold nerve injury: Observations in the rat." Brain. 120; pp. 631-646. 1997.
Jia, Jianping et al. "Cold injury to nerves is not due to ischaemia alone." Brain. 121;pp. 989-1001. 1998.
Jin, Yuanzhe. et al. "Pulmonary Vein Stenosis and Remodeling After Electrical Isolation for Treatment of Atrial Fibrillation: Short- and Medium-Term Follow-Up." PACE, vol. 27. pp. 1362-1370. Oct. 2004.

(56) References Cited

OTHER PUBLICATIONS

Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.
Jorgensen, William A. et al., "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.
Joshi, R.P. et al., "Improved energy model for membrane electroporation in biological cells subjected to electical pulses," Apr. 9, 2002, Physical Review E, vol. 65, 041920-1, © 2002 The American Physical Society, 8 pages.
Joshi, R.P. et al., "Self-consistent simulations of elctroporation dynamics in biological cells subjected to ultrashort electrical pulses," Jun. 21, 2001, Physical Review E, vol. 64, 011913, © 2001The American Physical Society, pp. 1-10.
Joshi, R.P., K.H. Schoenbach, "Mechanism for membrane electroporation irreversibility under high-intensity, ultrashort electrical pulse conditions," Nov. 11, 2002, Physical Review 2002, E 66, © 2002 The American Physical Society, pp. 052901-1-052901-4.
Joye, James D. And Tatsutani, Kristine. "In Vitro Studies of Arterial Freezing Injury". 4 pages.
Joye, James D. And Tatsutani, Kristine. "In Vivo Study of Endovascular Cryotherapy for the Prevention of Restenosis." 4 pages.
Kanduser, Masa et al., "Effect of surfactant polyoxyethylene glycol ($C_{12}E_8$) on electroporation of cell line DC3F," Aug. 20, 2002, Colloids and Surfaces A: Physiochem. Eng. Aspects 2003, vol. 214, © 2002 Elsevier Science B.V., pp. 205-217.
Katholi, Richard E., "Renal nerves in the pathogenesis of hypertension in experimental animals and humans," Am J Physiol., vol. 245, © 1983 the American Physiological Society, pp. F1-F14.
Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.
King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.
Kinney, Brian M., M.D., "High-Tech Healing—The evolution of therapeutic electromagnetic fields in plastic surgery," Plastic Surgery Products, Jun. 2004, pp. 32-36, 3 pages.
Knot, Harm J. And Nelson, Mark T. "Regulation of arterial diameter and wall [Ca2+] in cerebral arteries of rat by membrane potential and intravascular pressure." The Journal of Physiology. 1998. 508; pp. 199-209.
Kok, Lai Chow et al. "Effect of Heating on Pulmonary Veins: How to Avoid Pulmonary Vein Stenosis." Journal of Cardiovascular Electrophysiology. vol. 14, No. 3, Mar. 2003. Pages 250-254.
Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.
Kon, Valentina, "Neural Control of Renal Circulation," Miner Electrolyte Metab 1989, vol. 15, © 1989 S. Karger AG, pp. 33-43.
Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.
Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.
Kumagai, K. et al. "New Approach to Pulmonary Vein Isolation for Atrial Fibrillation Using a Multielectrode Basket Catheter". Circuation Journal. vol. 70, No. 1. Jan. 2006. Abstract only. 2 pages.
Lafayette, Richard A., M.D., "How Does Knocking Out Angiotensin II Activity Reduce Renal Injury in Mice?" Jun. 14, 1999, Journal Club, American Journal of Kidney Diseases, vol. 35, No. 1, Jan. 2000, © 2000 National Kidney Foundation Inc., pp. 166-172.
Lavie, Peretz, Ph.D. And Victor Hoffstein, M.D., "Sleep Apnea Syndrome: A Possible Contributing Factor to Resistant Hypertension," Jun. 2001, Sleep 2001, vol. 24, No. 6, pp. 721-725.
Lee, Michael A. (editor). SPORTSMed. Connecticut State Medical Society Committee on the Medical Aspects of Sports. Fall/Winter 2005. 10 pages.
Lee, Raphael C. and Jurgen Hannig, "Membrane Biology and Biophysics," Chapter 25, Surgical Research, © 2001 Academic Press, pp. 297-305.
Lee, Raphael C. et al., "Biophysical Injury Mechanisms in Electrical Shock Trauma," Annu. Rev. Biomed. Eng., 2000, vol. 02, Copyright © 2000 by Annual Reviews, pp. 477-509.
Lee, Raphael C. et al., "Clinical Sequelae Manifested in Electrical Shock Survivors," Presentation by the Electrical Trauma Research Program, The University of Chicago, 37 pages.
Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.
Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, © 1999 Massachusetts Medical Society, pp. 1321-1328.
Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.
Lipfert, Peter, M.D. et al., "Tachyphylaxis to Local Anesthetics Does Not Result From Reduced Drug Effectiveness at the Nerve Itself," Aug. 3, 1988, Anesthesiology 1989, vol. 70, pp. 71-75.
Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.
Lohmeier, Thomas E. and Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.
Lohmeier, Thomas E. et al., "Prolonged Activation of the Baroflex Produces Sustained Hypotension," Harry Goldblatt Award, Nov. 26, 2003, Hypertension 2004, vol. 43, part 2, © 2004 American Heart Association, Inc., pp. 306-311.
Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.
Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, © 2001 the American Physiological Society, pp. R434-R443.
Lohmeier, Thomas E., "Interactions Between Angiotensin II and Baroreflexes in Long-Term Regulation of Renal Sympathetic Nerve Activity," Circulation Research, Jun. 27, 2003, © 2003 American Heart Association Inc., pp. 1282-1284.
Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.
Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.
MacArthur, Dr. Alison, "Spinal Anesthesia and Severe Gestational Hypertension," presentation at Mount Sinai Hospital, 25 pages.
Maeder, Micha, M.D. et al., "Contrast Nephropathy: Review Focusing on Prevention," Jun. 22, 2004, Journal of the American College of Cardiology Nov. 2, 2004, vol. 44, No. 9, © 2004 by the American College of Cardiology Foundation, pp. 1763-1771.

(56) References Cited

OTHER PUBLICATIONS

Malpas, Simon C., "What sets the long-term level of sympathetic nerve activity: is there a role for arterial baroreceptors?" Invited Review, Am J Physiol Regul. Integr. Comp. Physiol. 2004, vol. 286, © 2004 the American Physiological Society, pp. R1-R12.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.

Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.

Mathur, Vandana S. "Intra-Renal Drug Delivery for Fluid Overload". FlowMedica. Transcatheter Cardiovascular Therapeutics 2005. 31 slides.

McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.

McCullough, Peter A., M.D., MPH et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.

McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.

McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.

Medtronic Neurostimulation Systems, "Expanding the Array of Pain Control Solutions," informational pamphlet, 1999 Medtronic, Inc., 6 pages.

Medtronic, "Spinal Cord Stimulation," Patient Management Guidelines for Clinicians, Medtronic, Inc. 1999, 115 pages.

Medtronic, "SynchroMed Infusion System —Clinical Reference Guide for Pain Therapy," Medtronic, Inc. 1998, 198 pages.

Mehran, Roxana. "Renal insufficiency and contrast nephropathy: The most common, least understood risk factor". Cardiovascular Research Foundation. Columbia University Medical Center. 2005. 86 slides.

Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.

Mihran, Richard T. et al., "Temporally-Specific Modification of Myelinated Axon Excitability in Vitro Following a Single Ultrasound Pulse," Sep. 25, 1989, Ultrasound in Med.& Biol. 1990, vol. 16, No. 3, pp. 297-309.

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba.

Mitchell, G.A.G., "The Nerve Supply of the Kidneys," Aug. 20, 1949, Acta Anatomica, vol. 10, Fasc. 1/2, 1950, pp. 1-37.

Moss, Nicholas G., "Renal function and renal afferent and efferent nerve activity," Am J Physiol 1982, vol. 243, © 1982, the American Physiological Society, pp. F425-F433.

Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.

Naropin (ropivacaine HCI) injection, Rx only description, AstraZeneca 2001, 3 pages.

National High Blood Pressure Education Program, "1995 Update of the Working Group Reports on Chronic Renal Failure and Renovascular Hypertension," presentation, 13 pages.

National Kidney Foundation, "Are You At Increased Risk for Chronic Kidney Disease?" © 2002 National Kidney Foundation, Inc., 14 pages.

Nelson, Lawrence D. and Jeffrey L. Osborn, "Neurogenic Control of Renal Function in Response to Graded Nonhypotensive Hemorrahage in Conscious Dogs," Sep. 13, 1992, Am. J. Physiol. 264, 1993, American Physiological Society 1993, pp. R661-R667.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Nozawa, Takashi et al., "Effects of Long Term Renal Sympathetic Denervation on Heart Failure After Myocardial Infarction in Rats," Sep. 22, 2001, Heart Vessels 2002, vol. 16, Springer-Verlag 2002, pp. 51-56.

Packer, Douglas L. et al. "Clinical Presentation, Investigation, and Management of Pulmonary Vein Stenosis Complicating Ablation for Atrial Fibrillation." Circulation: Journal of the American Heart Association. Feb. 8, 2005. pp. 546-554.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Pappone, Carlo and Santinelli, Vincenzo. "[2005][P2-70] Safety Report of Circumferential Pulmonary Vein Ablation. A 9-Year Single-Center Experience on 6,442 Patients with Atrial Fibrillation." Abstract only. 1 page.

Pappone, Carlo and Santinelli, Vincenzo. "Multielectrode basket catheter: A new tool for curing atrial fibrillation?" Heart Rhythm, vol. 3, Issue 4, pp. 385-386. Apr. 2006.

Pappone, Carlo et al. "[2004][759] Pulmonary Vein Denervation Benefits Paroxysmal Atrial Fibrillation Patients after Circumferential Ablation." Abstract only. 1 page.

Peacock, J.M. and R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Podhajsky, R. J., et al. "The Histologic Effects of Pulsed and Continuous Radiofrequency Lesions at 42° C to Rat Dorsal Root Ganglion and Sciatic Nerve," Spine, vol. 30, No. 9, 2005, Lippincott Williams & Wilkins Inc., pp. 1008-1013.

Pope, Jill. "Fixing a Hole: Treating Injury by Repairing Cells." Annals of the New York Academy of Sciences: Annals Extra. Jul. 6, 2006. 5 pages.

Popovic, Jennifer .R. and Margaret J. Hall," 1999 National Hospital Discharge Survey," Advance Data, No. 319, CDC, pp. 1-17 & 20.

Practice Guidelines Writing Committee and ESH/ESC Hypertension Guidelines Committee, "Practice Guidelines for Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Purerfellner, Helmut and Martinek, Martin. "Pulmonary vein stenosis following catheter ablation of atrial fibrillation." Current Opinion in Cardiology. 20; pp. 484-490. 2005.

Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.

Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

(56) References Cited

OTHER PUBLICATIONS

Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.

Ravalia, A. et al., "Tachyphylaxis and epidural anesthesia," Edgware General Hospital, Correspondence, p. 529.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Rump, L.C., "The Role of Sympathetic Nervous Activity in Chronic Renal Failure," J Clinical Basic Cardiology 2001, vol. 4, pp. 179-182.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.

Sabbah, Hani N. "Animal Models for Heart Failure and Device Development". Henry Ford Health System. 24 slides.

Schauerte, P et al. "Catheter ablation of cardiac autonomic nerves for prevention of vagal atrial fibrillation." Circulation. 102(22). Nov. 28, 2000. Abstract only. 2 pages.

Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.

Schauerte, P et al. "Transvenous parasympathetic nerve stimulation in the inferior vena cava and atrioventricular conduction." Journal of Cardiovascular Electrophysiology. 11(1). Jan. 2000. Abstract only. 2 pages.

Scheiner, Avram, Ph.D., "The design, development and implementation of electrodes used for functional electrical stimulation," Thesis paper, Case Western Reserve University, May 1992, 220 pages.

Scherlag, BJ and Po, S. "The intrinsic cardiac nervous system and atrial fibrillation." Current Opinion in Cardiology. 21(1):51-54, Jan. 2006. Abstract only. 2 pages.

Schmitt, Joseph et al. "Intravascular Optical Coherence Tomography—Opening a Window into Coronary Artery Disease". LightLab Imaging, Inc. Business Briefing: European Cardiology 2005.

Schoenbach, Karl H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Scremin, Oscar U., M.D., Ph.D. and Danel P. Holschneider, M.D., "31. & 32. An Implantable Bolus Infusion Pump for the Neurosciences," FRP, 04-05, 3 pages.

Serrador, Jorge M. "Autonomic Regulation of the Cardiovascular System". MIT Lecture. 8 pages, 48 slides.

Shu-Qing, Liu et al., "Old spinal cord injury treated by pulsed electric stimulation," General Hospital of Beijing Command, Beijing, 5 pages (full article in Chinese; abstract on last page).

Shupak, Naomi M., "Therapeutic Uses of Pulsed Magnetic-Field Exposure: A Review," Radio Science Bulletin Dec. 2003, No. 307, pp. 9-32.

Siegel, RJ et al. "Clinical demonstration that catheter-delivered ultrasound energy reverses arterial vasoconstriction." Journal of the American College of Cardiology. 1992. 20; 732-735. Summary only. 2 pages.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., " Effect of chronic bupivacaine infusion on seizure threshold to bupivacaine," Dec. 28, 1986, Acta Anaesthesiol. Scand. 1987, vol. 31, pp. 423-425.

Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.

Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: The Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "Radiofrequency Part 2: Thoracic and Cervical Region, Headache and Facial Pain," various pages from, FlivoPress SA, Meggen (LU), Switzerland, 13 pages.

Sluijter, M.D., Ph.D., "The Role of Radiofrequency in Failed Back Surgery Patients," Current Review of Pain 2000, vol. 4, © 2000 by Current Science Inc., pp. 49-53.

Sobotka, Paul A. "Treatment Strategies for Fluid Overload, CHF Patients". CHF Solutions. Transcatheter Cardiovascular Therapeutics 2005. 20 slides.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Steffen, W. et al. "Catheter-delivered high intensity, low frequency ultrasound induces vasodilation in vivo." European Heart Journal. 1994. 15;pp. 369-376.

Steg, PG et al. "Pulsed ultraviolet laser irradiation produces endothelium-independent relaxation of vascular smooth muscle". Circulation: Journal of the American Heart Association. 1989. pp. 189-197.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

(56) References Cited

OTHER PUBLICATIONS

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002. Pages 184-189.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14; pp. 41-25. 2005.

Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.

Terashima, Mitsuyasu et al. "Feasibility and Safety of a Novel CryoPlasty™ System". Poster. 1 page.

Thomas, John R. and Oakley, E. Howard N. "Chapter 15: Nonfreezing Cold Injury" *Medical Aspects of Harsh Environments*, vol. 1. pp. 467-490.

Thompson, Gregory W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.

Trapani, Angelo J. et al., "Neurohumoral interactions in conscious dehydrated rabbit," Am J Physiol 1988, vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.

United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," Jan. 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association—European Dialysis and Transplant Association, p. 160.

Van Antwerp, Bill and Poonam Gulati., "Protein Delivery from Mechanical Devices Challenges and Opportunities," Medtronic Presentation, 19 pages.

Velazquez, Eric J., "An international perspective on heart failure and left ventricular systolic dysfunction complicating myocardial infarction: the VALIANT registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Vigilance, Deon W. et al., "A Novel Approach to Increase Total Urine Output in Acute Heart Failure: Unilateral Renal nerve Blockade," RNB Abstract AHA, 2 pages.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Vince, D. Geoffrey. "Virtual Histology: A new technique for the assessment of plaque composition". The Cleveland Clinic Foundation. 28 pages.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Chapter 1: Electroporation Theory, Concepts and Mechanisms," Methods in Molecular Biology, vol. 55, Plant Cell Electroporation and Electrofusion Protocols, Edited by J.A. Nickoloff, © Humana Press Inc., pp. 3-28.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), © 2005 Sage Publications, pp. 63-75.

Wilson, D.H. et al., "The Effects of Pulsed Electromagnetic Energy on Peripheral Nerve Regeneration," Annals New York Academy of Sciences, pp. 575-585.

Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, © 2004 by Excerpta Medica, Inc., pp. 1526-1528.

Ye, Richard D., M.D., Ph.D., "Pharmacology of the Peripheral Nervous System," E-425 MSB, 6 pages.

Ye, Shaohua et al., "Renal Injury Caused by Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

(56) References Cited

OTHER PUBLICATIONS

Yong-Quan, Dong et al., "The therapeutic effect of pulsed electric field on experimental spinal cord injury," Beijing Army General Hospital of People's Liberation Army, Beijing, 5 pages (full article in Chinese; abstract on last page).
Young, James B., M.D., FACC, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.
Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.
Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.
Zimmermann, Ulrich, "Electrical Breakdown, Electropermeabilization and Electrofusion," Rev. Physiol. Biochem. Pharmacol., vol. 105, © Springer-Verlag 1986, pp. 175-256.
Zucker, Irving H. et al., "The origin of sympathetic outflow in heart failure: the roles of angiotensin II and nitric oxide," Progress in Biophysics & Molecular Biology 2004, vol. 84, © 2003 Elsevier Ltd., pp. 217-232.
Zundert, Jan Van, M.D. Fipp and Alex Cahana, M.D. DAAPM, "Pulsed Radiofrequency in Chronic Pain Management: Looking for the Best Use of Electrical Current," Pain Practice 2005, vol. 5, Issue 2, © 2005 World Institute of Pain, pp. 74-76.
U.S. Appl. No. 11/363,867, Demarais et al.
U.S. Appl. No. 11/504,117, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
Schneider, Peter A., "Endovascular Skills—Guidewire and Catheter Skills for Endovascular Surgery," Second Edition Revised and Expanded, 10 pages, (2003).
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N. V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 am, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.

(56) References Cited

OTHER PUBLICATIONS

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Millard, F. C., et al, "Renal Embolization for ablation of function in renal failure and hypertension." Postgraduate Medical Journal, 65, 729-734, (1989).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stouffer, G. A. et al., Journal of Molecular and Cellular Cardiology, vol. 62, 2013, 6 pages.

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Wilcox, Josiah N., Scientific Basis Behind Renal Denervation for the Control of Hypertension, ICI 2012, Dec. 5-6, 2012. 38 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

European Search Report for European Application No. 13159256, Date Mailed: Oct. 17, 2013, 6 pages.

Aggarwal, A. et al., Regional sympathetic effects of low-dose clonidine in heart failure. Hypertension. 2003;41:553-7.

Alexander, B.T. et al., Renal denervation abolishes hypertension in low-birth-weight offspring from pregnant rats with reduced uterine perfusion, Hypertension, 2005; 45 (part 2): 754-758.

Allen, E.V., Sympathectomy for essential hypertension, Circulation, 1952, 6:131-140.

Barajas, L. Innervation of the renal cortex. Fex Proc. 1978;37:1192-201.

Bello-Reuss, E. et al., Acute unilateral renal denervation in rats with extracellular volume expansion, Departments of Medicine and Physiology, University of North Carolina School of Medicine. F26-F32 Jul. 1975.

Bello-Reuss, E. et al., Effect of renal sympathetic nerve stimulation on proximal water and sodium reabsorption, J Clin Invest, 1976;57:1104-1107.

Bello-Reuss, E. et al., Effects of Acute Unilateral Renal Denervation in the Rat, J Clin Invest, 1975;56:208-217.

Bhandari, A. and Ellias, M., Loin pain hematuria syndrome: Pain control with RFA to the Splanchanic plexus, The Pain Clinic, 2000, vol. 12, No. 4, pp. 323-327.

Bichet, D., et al., Renal intracortical blood flow and renin secretion after denervation by 6-hydroxydopamine. Can J Physiol Pharmacol. 1982;60:184-92.

Bravo, E.L., et al., Renal denervation for resistant hypertension, American Journal of Kidney Diseases, 2009, 3 pgs.

Burns, J. et al., Relationship between central sympathetic drive and magnetic resonance imaging-determined left ventricular mass in essential hypertension. Circulation. 2007;115:1999-2005.

Campese, V.M. et al., Renal afferent denervation prevents hypertension in rats with chronic renal failure. Hypertension. 1995;25:878-82.

Campese, V.M., Neurogenic factors and hypertension in renal disease. Kidney Int. 2000;57 Suppl 75:S2-3.

Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.

Chin, J.L. et al., Renal autotransplantation for the loin pain-hematuria syndrome: long term follow up of 26 cases, J Urol, 1998, vol. 160, pp. 1232-1236.

Curtis, J.J. et al., Surgical theray for persistent hypertension after renal transplantation, Transplantation, 1981, 31(2):125-128.

Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.

Dibona, Gerald F., L.L. Sawin, Effect of renal nerve stimulation on NaCl and H2O transport in Henle's loop of the rat,: 1982, American Physiological Society, F576-F580, 5 pgs.

Esler, M. et al., Mechanism of elevated plasma noradrenaline in the course of essential hypertension. J Cardiovasc Pharmacol. 1986;8:S39-43.

Esler, M. et al., Noradrenaline release and the pathophysiology of primary human hypertension. Am J Hypertens. 1989; 2:140S-146S.

Esler, M. et al., Sympathetic nerve biology in essential hypertension, Clin and Exp Pharmacology and Physiology, 2001, 28:986-989.

European Examination Report; European Patent Application No. 07799148.7; Applicant: Ardian, Inc.; Date of Mailing: Jan. 19, 2010, 4 pgs.

European Examination Report; European Patent Application No. 09156661.2; Applicant: Ardian, Inc.; Date of Mailing: Jan. 19, 2010, 6 pgs.

European Search Report; European Patent Application No. 07798341.9; Applicant: Ardian, Inc.; Date of Mailing Aug. 4, 2011; 6 pgs.

Evelyn, K.A. et al., Effect of thoracolumbar sympathectomy on the clinical course of primary (essential) hypertension, Am J Med, 1960;28:188-221.

*Ex parte Quayle* Office Action; U.S. Appl. No. 11/144,173; Mailed on May 28, 2009, 4 pgs.

Fajardo, J. et al., Effect of chemical sympathectomy on renal hydroelectrolytic handling in dogs with chronic caval constriction. Clin Physiol Biochem. 1986;4:252-6.

Final Office Action; U.S. Appl. No. 11/233,814; Mailed on Jan. 29, 2009, 11 pgs.

Final Office Action; U.S. Appl. No. 11/266,993; Mailed on Jan. 8, 2010, 7 pgs.

Final Office Action; U.S. Appl. No. 11/363,867; Mailed on May 1, 2009, 8 pgs.

Final Office Action; U.S. Appl. No. 11/451,728; Mailed on Jan. 13, 2009, 7 pgs.

Final Office Action; U.S. Appl. No. 11/599,723; Mailed on Apr. 5, 2010, 17 pgs.

Final Office Action; U.S. Appl. No. 11/599,890; Mailed on Apr. 29, 2009, 9 pgs.

(56) References Cited

OTHER PUBLICATIONS

Gazdar, A.F. And G.J. Dammin, Neural degeneration and regeneration in human renal transplants, NEJM, Jul. 30, 1970, 283:222-244.
Getts, R.T. et al., Regression of left ventricular hypertrophy after bilateral nephrectomy, Nephrol Dial Transplant, 2006, vol. 21, pp. 1089-1091.
Gottschalk, C.W., Renal nerves and sodium excretion, Ann. Rev. Physiol., 1979, 41:229-240.
Haissaguerre, M. et al., Spontaneous initiation of atrial fibrillation by ectopic beats orginating in the pulmonary veins, New England Journal of Medicine, 1998, 339: 659-666.
Hampers, C.L. et al., A hemodynamic evaluation of bilateral nephrectomy and hemodialysis in hypertensive man, Circulation. 1967;35:272-288.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heuer, G.J., The surgical treatment of essential hypertension, Annals of Surgery, 1936; 104 (4): 771-786.
Implantable Neurostimulation Systems, Medtronic Neurological, http://medtronic.com/neuro/paintherapies/pain_treatment_ladder/pdf/implantable_brochure.pdf.
International Search Report, PCT/US02/0039, Mailed Sep. 11, 2002, Applicant: Advanced Neuromodulation Systems, Inc.
International Search Report, PCT/US02/25712, Mailed on Apr. 23, 2003, Applicant: Cyberonics, Inc.
International Search Report, PCT/US03/08014, Mailed on Sep. 23, 2003, Applicant: The General Hospital Corporation.
International Search Report, PCT/US03/09764, Mailed on Oct. 28, 2003, Applicant: CVRX, Inc.
Joles, J.A. et al., Causes and Consequences of Increased Sympathetic Activity in Renal Disease. Hypertension. 2004;43:699-706.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II):II-166-11-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Kaye, D.M. et al., Functional and neurochemical evidence for partial cardiac sympathetic reinnervation after cardiac transplantation in humans, Circulation, 1993, vol. 88, pp. 1101-1109.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lenoble, L.M. et al., Selective efferent chemical sympathectomy of rat kidneys. Am J Physiol. 1985;249:8496-501.
Luippold, G. et al., Chronic renal denervation prevents glomerular hyperfiltration in diabetic rats, Nephrol Dial Transplant (2004) 19:342-347.
Mancia, G., Grassi, G., Giannattasio, C., Seravalle, G., Sympathetic actrivation of pathogenesis of hypertension and progression of organ damage, Hypertension 1999, 34 (4 Pt 2): 724-728.
Medtronic Inc., MiniMed 2007, Implantable Insulin Pump System (Shoreview, MN) 4 pgs.
Morrisey, D.M. et al., Sympathectomy in the treatment of hypertension: Review of 122 cases, Lancet. 1953;1:403-408.
Non-Final Office Action; U.S. Appl. No. 10/408,665; Mailed on Mar. 21, 2006, 14 pgs.
Non-Final Office Action; U.S. Appl. No. 11/129,765; Mailed on May 18, 2007, 10 pgs.
Non-Final Office Action; U.S. Appl. No. 11/129,765; Mailed on Sep. 10, 2007, 5 pgs.
Non-Final Office Action; U.S. Appl. No. 11/129,765; Mailed on Oct. 6, 2006, 30 pgs.
Non-Final Office Action; U.S. Appl. No. 11/133,925; Mailed on Oct. 8, 2008, 41 pgs.
Non-Final Office Action; U.S. Appl. No. 11/144,173; Mailed on Apr. 5, 2007, 33 pgs.
Non-Final Office Action; U.S. Appl. No. 11/144,173; Mailed on Sep. 10, 2007, 5 pgs.
Non-Final Office Action; U.S. Appl. No. 11/144,298; Mailed Oct. 29, 2009, 8 pgs.
Non-Final Office Action; U.S. Appl. No. 11/144,298; Mailed on Apr. 5, 2007, 33 pgs.
Non-Final Office Action; U.S. Appl. No. 11/144,298; Mailed on Sep. 10, 2007, 5 pgs.
Non-Final Office Action; U.S. Appl. No. 11/144,298; Mailed on Dec. 29, 2008, 7 pgs.
Non-Final Office Action; U.S. Appl. No. 11/145,122; Mailed on Apr. 11, 2007, 33 pgs.
Non-Final Office Action; U.S. Appl. No. 11/145,122; Mailed on Sep. 10, 2007, 5 pgs.
Non-Final Office Action; U.S. Appl. No. 11/189,563; Mailed on May 28, 2009, 5 pgs.
Non-Final Office Action; U.S. Appl. No. 11/233,814; Mailed on Jun. 17, 2008, 12 pgs.
Non-Final Office Action; U.S. Appl. No. 11/252,462; Mailed on Feb. 22, 2010, 6 pgs.
Non-Final Office Action; U.S. Appl. No. 11/266,993; Mailed on Jul. 8, 2009, 5 pgs.
Non-Final Office Action; U.S. Appl. No. 11/266,993; Mailed on Dec. 30, 2008, 7 pgs.
Non-Final Office Action; U.S. Appl. No. 11/363,867; Mailed on Sep. 25, 2008, 10 pgs.
Non-Final Office Action; U.S. Appl. No. 11/368,553; Mailed on May 18, 2010, 4 pgs.
Non-Final Office Action; U.S. Appl. No. 11/368,553; Mailed on Oct. 7, 2009, 5 pgs.
Non-Final Office Action; U.S. Appl. No. 11/368,809; Mailed on Dec. 3, 2009, 4 pgs.
Non-Final Office Action; U.S. Appl. No. 11/368,949; Mailed on Jun. 11, 2010, 6 pgs.
Non-Final Office Action; U.S. Appl. No. 11/368,971; Mailed on Aug. 24, 2010, 9 pgs.
Non-Final Office Action; U.S. Appl. No. 11/451,728; Mailed on Jun. 12 2008, 41 pgs.
Non-Final Office Action; U.S. Appl. No. 11/451,728; Mailed on Jul. 2, 2009, 5 pgs.
Non-Final Office Action; U.S. Appl. No. 11/451,728; Mailed on Dec. 28, 2009, 7 pgs.
Non-Final Office Action; U.S. Appl. No. 11/504,117; Mailed on Mar. 31, 2009, 10 pgs.
Non-Final Office Action; U.S. Appl. No. 11/599,649; Mailed on Mar. 30, 2009, 10 pgs.
Non-Final Office Action; U.S. Appl. No. 11/599,649; Mailed on Jun. 23, 2008, 9 pgs.
Non-Final Office Action; U.S. Appl. No. 11/599,723; Mailed on Jun. 26, 2009, 17 pgs.

(56) References Cited

OTHER PUBLICATIONS

Non-Final Office Action; U.S. Appl. No. 11/599,723; Mailed on Oct. 15, 2010, 16 pgs.
Non-Final Office Action; U.S. Appl. No. 11/599,882; Mailed on Jul. 6, 2009, 13 pgs.
Non-Final Office Action; U.S. Appl. No. 11/688,178; Mailed on Jun. 28, 2010, 5 pgs.
Non-Final Office Action; U.S. Appl. No. 11/840,142; Mailed on Apr. 3, 2009, 13 pgs.
Non-Final Office Action; U.S. Appl. No. 12/567,521; Mailed on Sep. 3, 2010, 9 pgs.
Non-Final Office Action; U.S. Appl. No. 12/616,708; Mailed Sep. 16, 2010, 10 pgs.
Non-Final Office Action; U.S. Appl. No. 12/725,375; Mailed on Oct. 12, 2010, 14 pgs.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Page, I.H. et al., The Effect of Renal Denervation on the Level of Arterial Blood Pressure and Renal Function in Essential Hypertension. J Clin Invest. 1935;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Petersson, M. et al., Long-term outcome in relation to renal sympathetic activity in patients with chronic heart failure. Eur Heart J. 2005;26:906-13.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Smithwick, R.H. et al., Hypertension and associated cardiovascular disease: comparison of male and female mortality rates and their influence on selection of therapy, JAMA, 1956, 160:1023-1033.
Smithwick, R.H. et al., Splanchnicectomy for essential hypertension, Journal Am Med Assn, 1953;152:1501-1504.
Smithwick, R.H., Surgical treatment of hypertension, Am J Med 1948, 4:744-759.
Solis-Herruzo, J.A. et al., Effects of lumbar sympathetic block on kidney function in cirrhotic patients with hepatorenal syndrome, Journal of Hepatology, 1987; 5: 167-173.
Strojek, K. et al., Lowering of microalbuminuria in diabetic patients by a sympathicoplegic agent: novel approach to prevent progression of diabetic nephropathy? J Am Soc Nephrol. 2001;12:602-5.
Vonend, O. et al., Moxonidine treatment of hypertensive patients with advanced renal failure. J Hypertens. 2003;21:1709-17.
Whitelaw, G.P., Kinsey, D., Smithwick, R.H., Factors influencing the choice of treatment in essential hypertension: surgical, medical, or a combination of both, Am J Surg, 1964, 107:220-231.
Ye, S. et al., A limited renal injury may cause a permanent form of neurogenic hypertension. Am J Hypertens. 1998;11:723-8.
Zanchetti, A. et al., Practice Guidelines for Primary Care Physicians: 2003 ESH/ESC Hypertension Guidelines, Journal of Hypertension, vol. 21, No. 10, 2003, pp. 1779-1786.
Zanchetti, A.S., Neural regulation of renin release: Experimental evidence and clinical implications in arterial hypertension, Circulation, 1977, 56(5) 691-698.
Zoccali, C. et al., Plasma norepinephrine predicts survival and incident cardiovascular events in patients with end-stage renal disease. Circulation. 2002;105:1354-9.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Blessing, Erwin et al., Cardiac Ablation and Renal Denervation Systems Have Distinct Purposes and Different Technical Requirements, JACC Cardiovascular Interventions, vol. 6, No. 3, 2013.
ClinicalTrials.gov, Renal Denervation in Patients with uncontrolled Hypertension in Chinese (2011), www.clinicaltrials.gov/ct2/show/NCT01390831.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hyptenion, Mar. 2013, http://clinicaltrials.gov/ct2/show/NCT01628198.
Prochnau, Dirk et al., Catheter-based renal denervation for drug-resistant hypertension by using a standard electrophysiology catheter; Euro Intervention 2012, vol. 7, pp. 1077-1080.
Schneider, Peter A.., "Endovascular Skills—Guidewires, Catheters, Arteriography, Balloon Angioplasty, Stents", pp. 70-71, 101 and 188-190 (1998).
ThermoCool Irrigated Catheter and Integrated Ablation System, Biosense Webster (2006).
Hall, W. H., et al. "Combined embolization and percutaneous radiofrequency ablation of a solid renal tumor." Am. J. Roentgenol,174: 1592-1594 (2000).
Hanson, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988).
Medical-Dictionary.com, Definition of "Animal Model," http://medical-dictionary.com (search "Animal Model"), 2005.
Medtronic, Inc., Annual Report (Form 10-K) (Jun. 28, 2011).
Ong, K. L., et al. "Prevalence, Awareness, Treatment, and Control of Hypertension Among United States Adults 1999-2004." Hypertension, 49: 69-75 (2007) (originally published online Dec. 11, 2006).
Renal Denervation (RDN), Symplicity RDN System Common Q&A (2011), http://www.medtronic.com/rdn/mediakit/RDN%20FAQ.pdf.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Avitall et al., "The creation of linear contiguous lesions in the atria with an expandable loop catheter,"Journal of the Americam College of Cardiology, 1999; 33; pp. 972-984.
Benito, F., et al. "Radiofrequency cateheter ablation of accessory pathways in infants." Heart, 78:160-162 (1997).
Dubuc, M., et al., "Feasibility of cardiac cryoablation using a transvenous steerable electrode catheter." J Interv Cardiac Electrophysiol, 2:285-292 (1998).
Excerpt of Operator's Manual of Boston Scientific's EPT-1000 XP Cardiac Ablation Controller & Accessories, Version of Apr. 2003, (6 pages).

(56) References Cited

OTHER PUBLICATIONS

Excerpt of Operator's Manual of Boston Scientific's Maestro 30000 Cardiac Ablation System, Version of Oct. 17, 2005 , (4 pages).
Gelfand, M., et al., "Treatment of renal failure and hypertension." U.S. Appl. No. 60/442,970.
Han, Y.-M, et al., "Renal artery ebolization with diluted hot contrast medium: An experimental study." J Vasc Interv Radiol, 12: 862-868 (2001).
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustrgarten, D.L.,et al., "Cryothermal ablation: Mechanism of tissue injury and current experience in the treatment of tachyarrhythmias." Progr Cardiovasc Dis, 41:481-498 (1999).
Oliverira, V., et al., "Renal denervation normalizes pressure and baroreceptor reflex in high renin hypertension in conscious rats." Hypertension, 19:II-17-II-21 (1992).
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Peet, M., "Hypertension and its Surgical Treatment by bilateral supradiaphragmatic splanchnicectomy" Am J Surgery (1948) pp. 48-68.
Schauerte, P., et al. "Catheter ablation of cardiac autonomic nerves for prevention of vagal atrial fibrillation." Circulation, 102:2774-2780 (2000).
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Weinstock, M., et al., "Renal denervation prevents sodium rentention and hypertension in salt sensitive rabbits with genetic baroreflex impairment." Clinical Science, 90:287-293 (1996).
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardian Electrophysiology, 2001, pp. 401-410.
U.S. Appl. No. 12/940,922, filed Nov. 5, 2010, Gelfand et al.
U.S. Appl. No. 12/790,639, filed May 28, 2010, Wu et al.
U.S. Appl. No. 12/871,457, filed Aug. 30, 2010, Wu et al.
U.S. Appl. No. 13/007,370, filed Jan. 18, 2011, Gelfand et al.
U.S. Appl. No. 12/996,897, filed Dec. 13, 2010, Demarais.
U.S. Appl. No. 13/009,748, filed Jan. 19, 2011, Beetel et al.
U.S. Appl. No. 12/910,631, filed Oct. 22, 2010, Wu et al.
International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report and Written Opinion for PCT/US2009/069334; Applicant: Ardian, Inc.; Mailing Date: Mar. 1, 2010, 10 pages.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant: Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Search Report; European Patent Application No. 09156661.2; Applicant: Ardian, Inc.; Date of Mailing: Jul. 23, 2009, 6 pages.
European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
European Search Report; European Patent Application No. 07868755.5; Applicant: Ardian, Inc.; Date of Mailing: Jul. 28, 2010, 7 pages.
Thatipelli et al., CT Angiography of Renal Artery Anatomy for Evaluating Embolic Protection Devices, Journal of Vascular and Interventional Radiology, Jul. 2007, pp. 842-846.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Oz, Mehmet, Pressure Relief, Time, Jan. 9, 2012, 2 pages. <www.time.come/time/printout/0,8816,2103278,00.html>.
Purerfellner, Helmut et al., Pulmonary Vein Stenosis Following Catheter Ablation of Atrial Fibrillation, Curr. Opin. Cardio. 20 :484-490, 2005.
Papademetriou, Vasilios, Renal Sympathetic Denervation for the Treatment of Difficult-to-Control or Resistant Hypertension, Int. Journal of Hypertension, 2011, 8 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Claudine Jaboro, "An in vivo study of the biocompatibility of classic and novel device materials on the central nervous system", (Jan. 1, 2007), ETD Collection for Wayne State University. Paper AA13310737. <http://digitalcommons.wayne.edu/dissertations/AA13310737>.

(56) References Cited

OTHER PUBLICATIONS

European Search Report dated Jan. 30, 2013; European Application No. 12180426.4; Applicant: Medtronic Ardian Luxembourg S.a.r.l.; 6 pages.

European Search Report dated Feb. 28, 2013; European Application No. 12180427.2; Applicant: Medtronic Ardian Luxembourg S.a.r.l.; 4 pages.

European Search Report dated Jan. 30, 2013; Application No. 12180428.0; Applicant: Medtronic Ardian Luxembourg S.a.r.l.; 6 pages.

European Search Report dated Jan. 30, 2013; Application No. 12180430.6; Applicant: Medtronic Ardian Luxembourg S.a.r.l.; 6 pages.

European Search Report dated Jan. 30, 2013; Application No. 12180431.4; Applicant: Medtronic Ardian Luxembourg S.a.r.l.; 6 pages.

European Search Report dated Feb. 22, 2013; Application No. 12180432.2; Applicant: Medtronic Ardian Luxembourg S.a.r.l.; 6 pages.

International Search Report and Written Opinion dated Jan. 23, 2012, International Application No. PCT/US2011/057761, 13 pages.

International Search Report and Written Opinion dated Jan. 20, 2012, International Application No. PCT/US2011/057756, 10 pages.

International Search Report and Written Opinion dated Feb. 16, 2012, International Application No. PCT/US2011/057754, 13 pages.

Lahiri D. et al. Boron nitride nanotube reinforced polylactide-polycaprolactone copolymer composite: Mechanical properties and cytocompatibility with osteoblasts and macrophages in vitro. Acta Biomater (2010), doi: 10.1016/j.actbio.2010.02.44.

Materials Research Society, "Biomedical Materials and Devices," Symposium helped Nov. 30-Dec. 4, 1987, Boston Massachusetts, USA.

European Search Report for European App. No. 11192514 Date Mailed: May 3, 2012 7 pages.

European Search Report for European App. No. 11192511 Mailed May 3, 2012, 6 pages.

European Search Report for European App. No. 12180432.2 mailed Apr. 18, 2013, 9 pages.

Eick Olaf "Temperature Controlled Radiofrequency Ablation." Indian Pacing and Electrophysiology Journal vol. 2. No. 3, 2002, 8 pages.

International Search Report, PCT/US02/07661, Aug. 13, 2002, 5 Pages.

International Search Report, PCT/US03/031339, Feb. 18, 2004, 3 Pages.

International Search Report, PCT/US01/044977, Jun. 7, 2002, 6 Pages.

\* cited by examiner

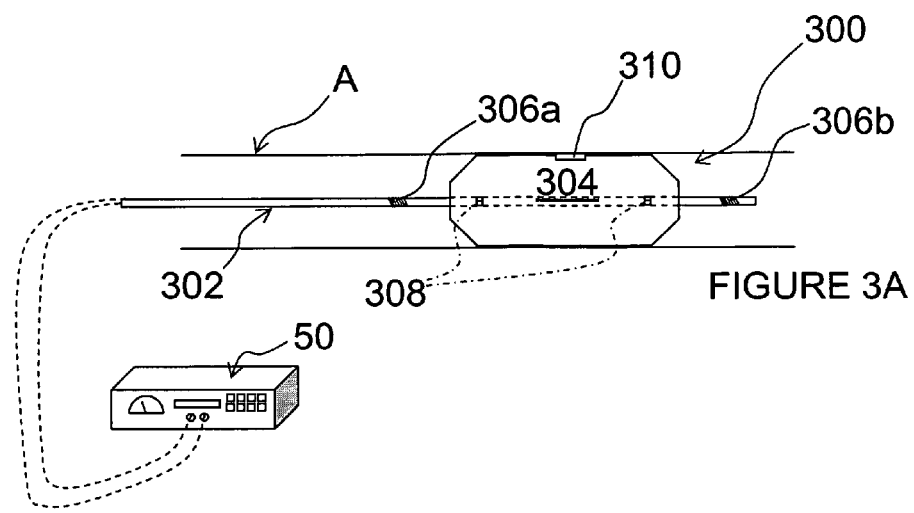
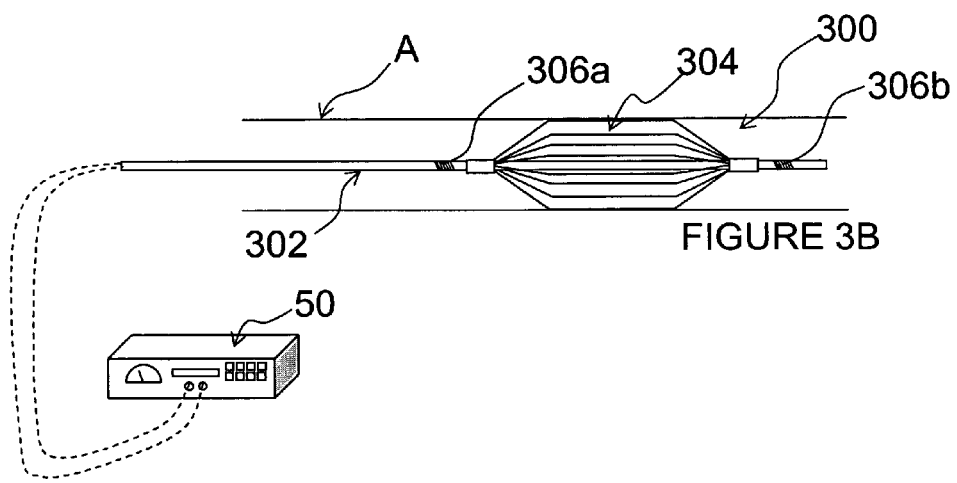

METHODS AND APPARATUS FOR INTRAVASCULARY-INDUCED NEUROMODULATION

REFERENCE TO RELATED APPLICATIONS

The present application is a continuation-in-part of U.S. patent application Ser. No. 11/363,867, filed on Feb. 27, 2006, now U.S. Pat. No. 7,620,451, which claims the benefit of U.S. Provisional Application No. 60/813,589, filed on Dec. 29, 2005 (originally filed as U.S. application Ser. No. 11/324, 188), both of which are incorporated by reference herein. Further, the present application is a continuation-in-part of each of the following U.S. patent applications:

(a) U.S. patent application Ser. No. 11/129,765, filed on May 13, 2005, now U.S. Pat. No. 7,653,438, which claims the benefit of U.S. Provisional Application Nos. 60/616,254, filed on Oct. 5, 2004; and 60/624,793, filed on Nov. 2, 2004, and is a continuation-in-part of U.S. patent application Ser. No. 10/408,665, filed on Apr. 8, 2003, now U.S. Pat. No. 7,162,303, which claims the benefit of U.S. Provisional Patent Application Nos. 60/442,970, filed on Jan. 29, 2003; 60/415,575, filed on Oct. 3, 2002; and 60/370,190, filed on Apr. 8, 2002.

(b) U.S. patent application Ser. No. 11/189,563 filed Jul. 25, 2005, now U.S. Pat. No. 8,145,316, which (a) is a continuation-in-part of U.S. patent application Ser. No. 11/129, 765, filed May 13, 2005, now U.S. Pat. No. 7,653,438, which claims the benefit of U.S. Provisional Patent Application Nos. 60/616,254, filed Oct. 5, 2004, and 60/624,793, filed Nov. 2, 2004; and (b) is a continuation-in-part of U.S. patent application Ser. No. 10/900,199, filed Jul. 28, 2004, now U.S. Pat. No. 6,978,174, which is a continuation-in-part of U.S. patent application Ser. No. 10/408,665, filed Apr. 8, 2003, now U.S. Pat. No. 7,162,303, which claims the benefit of U.S. Provisional Application Nos. 60/370,190 filed Apr. 8, 2002; 60/415,575, filed Oct. 3, 2002; and 60/442,970, filed Jan. 29, 2003.

(c) U.S. patent application Ser. No. 11/403,329, filed Apr. 13, 2006, now U.S. Pat. No. 8,131,371, which (a) is a continuation-in-part of U.S. patent application Ser. No. 11/129, 765, filed May 13, 2005, now U.S. Pat. No. 7,653,438, which claims the benefit of U.S. Provisional Patent Application Nos. 60/616,254, filed Oct. 5, 2004, and 60/624,793, filed Nov. 2, 2004; and (b) is a continuation-in-part of U.S. patent application Ser. No. 10/408,665, filed Apr. 8, 2003, now U.S. Pat. No. 7,162,303, which claims the benefit of U.S. Provisional Application Nos. 60/370,190 filed Apr. 8, 2002; 60/415,575, filed Oct. 3, 2002; and 60/442,970, filed Jan. 29, 2003; and (c) is a continuation-in-part of U.S. patent application Ser. No. 11/189,563, filed Jul. 25, 2005, now U.S. Pat. No. 8,145,316; and (d) is a continuation-in-part of U.S. patent application Ser. No. 11/266,993, filed Nov. 4, 2005, now U.S. Pat. No. 7,756,583; and (e) is a continuation-in-part of U.S. patent application Ser. No. 11/363,867, filed Feb. 27, 2006, now U.S. Pat. No. 7,620,451.

(d) U.S. patent application Ser. No. 11/504,117, filed Aug. 14, 2006, now U.S. Pat. No. 7,617,005, which (a) is a continuation-in-part of U.S. patent application Ser. No. 10/408, 665, filed Apr. 8, 2003, now U.S. Pat. No. 7,617,005, which claims the benefit of U.S. Provisional Application Nos. 60/370,190 filed Apr. 8, 2002; 60/415,575, filed Oct. 3, 2002; and 60/442,970, filed Jan. 29, 2003; and (b) is a continuation-in-part of U.S. patent application Ser. No. 11/189,563, filed Jul. 25, 2005, now U.S. Pat. No. 8,145,316, which is a continuation-in-part of U.S. patent application Ser. No. 11/129, 765, filed May 13, 2005, now U.S. Pat. No. 7,653,438, which claims the benefit of U.S. Provisional Patent Application Nos. 60/616,254, filed Oct. 5, 2004, and 60/624,793, filed Nov. 2, 2004

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. Several embodiments, more particularly, relate to intravascular methods and apparatus for denervating a desired innervated blood vessel in a patient, or a target nerve or nervous tissue (e.g., brain tissue) in proximity to the blood vessel in order to treat any neurological disorder or other medical condition.

BACKGROUND

Applicants have described methods and apparatus for treating a variety of renal and cardio-renal diseases, such as congestive heart failure ("CHF"), renal disease, renal failure, hypertension, heart arrhythmia and myocardial infarction, by modulating or denervating neural fibers that contribute to renal function. This reduces renal sympathetic nervous activity, which increases removal of water and sodium from the body, and returns renin secretion to more normal levels. Normalized renin secretion may normalize renal blood flow and decrease peripheral vascular resistance. See, for example, Applicants' co-pending U.S. patent application Ser. No.: (a) 10/408,665, filed Apr. 8, 2003; (b) Ser. No. 11/129,765, filed on May 13, 2005; (c) Ser. No. 11/189,563, filed on Jul. 25, 2005; (d) Ser. No. 11/363,867, filed on Feb. 27, 2006; (e) Ser. No. 11/504,117, filed on Aug. 14, 2006; as well as U.S. Pat. No. 6,978,174. All of these applications and the patent are incorporated herein by reference in their entireties.

Many blood vessels throughout the body are innervated. Furthermore, many nerves travel in proximity to blood vessels of the body. In some patients, it may be desirable to modulate such nerves or nervous tissue (e.g., brain tissue) within or in proximity to a blood vessel to treat a neurological disorder or other medical condition. Such modulation may desirably result in alteration of the nerve function or denervation of tissue that is innervated by the nerves. However, it may be invasive or impractical to access such nerves/nervous tissue, or it may be difficult to locally modulate the nerves or denervate target tissue without excessively damaging surrounding tissues. Therefore, it would be desirable to provide methods and apparatus for intravascularly-induced denervation.

BRIEF DESCRIPTION OF THE DRAWINGS

Several embodiments will be apparent upon consideration of the following detailed description, taken in conjunction with the accompanying drawings, in which like reference characters refer to like parts throughout, and in which:

FIGS. 3A and 3B are schematic side views, partially in section, illustrating examples of intravascular methods and apparatus for neuromodulation or denervation.

DETAILED DESCRIPTION

A. Overview

Figure 1:
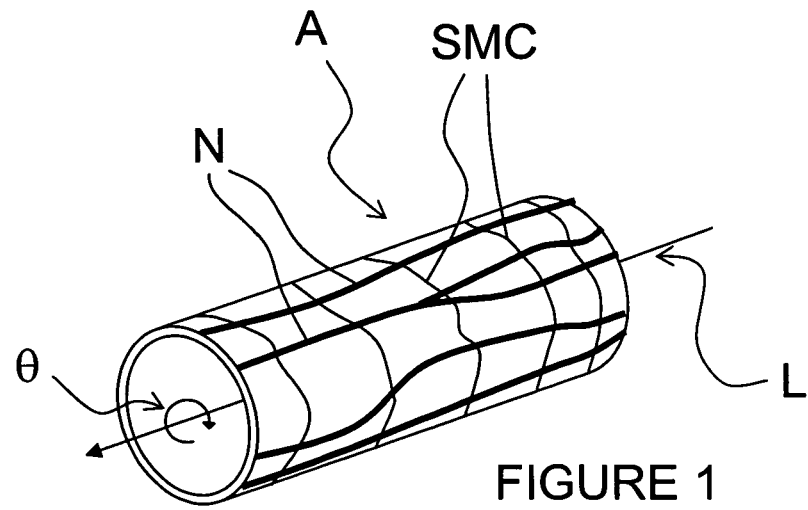
FIG. 1 is a schematic isometric detail view showing a common location of neural fibers proximate an artery.

Several embodiments of the methods and apparatus described below provide intravascularly-induced neuromodulation or denervation of an innervated blood vessel in a patient, target neural fibers, or other neural tissue (e.g., brain tissue) in proximity to a blood vessel. The disclosed methods and apparatus can be used to treat any neurological disorder or other medical condition. Nerves in proximity to a blood vessel may innervate or otherwise affect an organ or tissue. Intravascularly-induced neuromodulation or denervation may be utilized to treat a host of neurological disorders or other medical conditions, including, but not limited to, heart failure, hypertension, renal disease, renal failure, contrast nephropathy, myocardial infarction, pain, heart arrhythmia, peripheral arterial occlusive disease (e.g., via pain mitigation), headache or migraine, spasticity, rigor, and cerebral palsy. Additional disorders and medical conditions for which the apparatus and methods may be utilized for treatment include, for example, conditions and disorders listed in Table 1 of United States Patent Application Publication Number US2006/0111754 to Rezai et al., which is incorporated herein by reference in its entirety. The methods and apparatus described herein may, for example, be used to modulate efferent nerves, afferent nerves, sympathetic nerves, parasympathetic nerves, sensory nerves, and/or motor nerves, as well as combinations thereof. In addition, the methods and apparatus described herein may, for example, be used to modulate brain tissue.

The intravascularly-induced neuromodulation or denervation may be achieved via apparatus percutaneously positioned within vasculature in proximity to target neural matter (e.g., neural fibers or neural tissue) for application of energy to the target neural matter. The neuromodulation or denervation may be induced, for example, via electrical energy application, via thermal energy application (either heating or cooling), via mechanical energy application, via chemical energy application, via radiation energy application, etc. Such neuromodulation may be achieved, for example, via (a) a thermal or non-thermal electric field, (b) a continuous or pulsed electric field, (c) a stimulation electric field, (d) localized drug delivery, (e) high intensity focused ultrasound, (f) thermal techniques, (g) athermal techniques, and/or (h) combinations thereof. Such neuromodulation may, for example, effectuate irreversible electroporation or electrofusion, necrosis and/or inducement of apoptosis, alteration of gene expression, action potential blockade or attenuation, changes in cytokine up-regulation, and other conditions in target neural matter. All or a part of the apparatus optionally may be passed through a wall of the vasculature to an extravascular location in order to facilitate the neuromodulation or denervation.

Neuromodulation or denervation may be achieved via either direct alteration of the target neural structures or at least in part via alteration of the vascular structures that support the target neural matter, such as arteries, arterioles, capillaries, veins or venules. In some embodiments, the neuromodulation or denervation may be achieved via direct application of energy to the target neural matter, or the vascular structures supporting the target neural matter. In other embodiments, the neuromodulation or denervation may be achieved via indirect generation and/or application of the energy, such as through application of an electric field or of high-intensity focused ultrasound that causes resistive heating in the target neural matter or the supporting vascular structures. Furthermore, the neuromodulation/denervation may at least in part be induced via irreversible electroporation of the target neural matter, or of the supporting structures.

In some embodiments, methods and apparatus for real-time monitoring of an extent or degree of neuromodulation or denervation in the target neural matter, or support structures, and/or of undesirable damage in the non-target tissue, may be provided. Likewise, real-time monitoring of the energy delivery apparatus may be provided. Power, total energy delivered, and/or temperature additionally or alternatively may be monitored.

When utilizing an electric field to achieve desired neuromodulation or denervation, the electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), power, etc. For example, suitable field strengths can be up to about 10,000 V/cm, and may be either continuous or pulsed. Suitable shapes of the electrical waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations thereof.

When utilizing a pulsed electric field, suitable pulse widths can be of any desired interval, for example, up to about 1 second. The field includes at least one pulse, and in many applications the field includes a plurality of pulses or is continuously applied, e.g., for up to several minutes. Suitable pulse intervals include, for example, intervals less than about 10 seconds. These parameters are provided as suitable examples and in no way should be considered limiting.

When utilizing thermal mechanisms to achieve the neuromodulation or denervation, protective elements optionally may be provided to protect the non-target tissue, such as the smooth muscle cells, from thermal damage during the thermally-induced neuromodulation or denervation. For example, when heating the nerves or support structures, protective cooling elements, such as convective cooling elements, may be provided to protect the non-target tissue. Likewise, when cooling the nerves or support structures, protective heating elements, such as convective heating elements, may be utilized to protect the non-target tissue. Thermal energy may be applied either directly or indirectly for a brief or sustained period of time in order to achieve desired neuromodulation or denervation. Feedback, such as sensed temperature along target or non-target tissue or along the device, optionally may be used to control and/or monitor delivery of the thermal energy.

The non-target tissue optionally may be protected during the neuromodulation or denervation by utilizing blood flow as a conductive and/or convective thermal sink that absorbs excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal energy or other energy on the target neural matter, or the support structures, such that an intensity of the energy is insufficient to induce thermal damage in the non-target tissue distant from the target neural matter.

Additional and alternative methods and apparatus may be utilized to achieve neuromodulation or denervation, as described hereinafter. To better understand the embodiments of methods and devices for intravascularly-induced neuromodulation or denervation described below, it is instructive to examine the neurovascular anatomy in humans.

B. Neurovascular Anatomy Summary

FIG. 1 illustrates a common anatomical arrangement of neural structures relative to vascular structures, typically arteries. Neural fibers N generally may extend longitudinally along the lengthwise dimension L of an artery A, often within the adventitia of the artery. The artery A has smooth muscle cells SMC that surround the arterial circumference and generally spiral around the angular dimension θ of the artery. The smooth muscle cells of the artery accordingly have a lengthwise or longer dimension generally extending transverse (i.e., non-parallel) to the lengthwise dimension of the blood vessel. The misalignment of the lengthwise dimensions of the neural fibers and the smooth muscle cells is defined as "cellular misalignment."

Figure 2A:
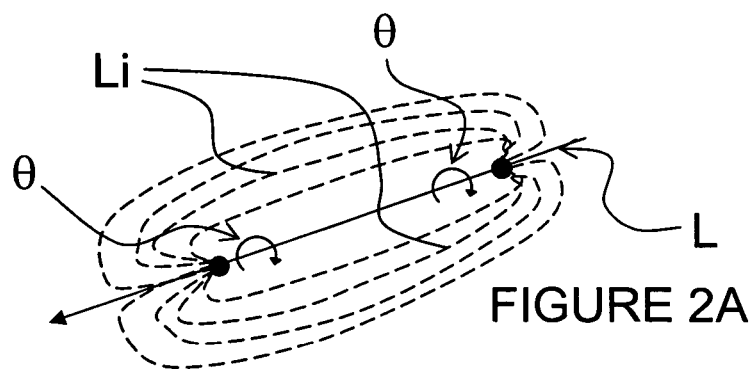
FIGS. 2A and 2B are schematic isometric and end views, respectively, illustrating orienting of an electric field for selectively affecting nerves positioned proximate an artery.
Figure 2B:
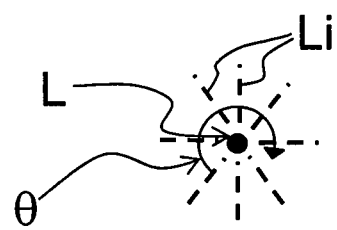

Referring to FIGS. 2A and 2B, the cellular misalignment of the nerves N and the smooth muscle cells SMC may be exploited to selectively affect the nerve cells with reduced effect on the smooth muscle cells. More specifically, energy application may be directed along the lengthwise dimension L of the artery A, rather than along the angular dimension θ of the artery.

For example, when utilizing electrical energy application to achieve the desired neuromodulation or denervation, it is known that larger cells require lower electric field strength to exceed the cell membrane irreversibility threshold voltage or energy for irreversible electroporation than do smaller cells. Thus, embodiments of electrodes of the present invention may be configured to align at least a portion of an electric field generated by the electrodes with or near the longer dimensions of the cells to be affected. In specific embodiments, the device has electrodes configured to create an electrical field aligned with or near the lengthwise dimension L of the artery A to affect nerves N. By aligning an electric field so that the field preferentially aligns with the lengthwise aspect of the nerve cells rather than the diametric or radial aspect of the cells, lower field strengths may be used to affect the target neural cells, e.g., to necrose or fuse the target cells, to induce apoptosis, to alter gene expression, to attenuate or block action potentials, to change cytokine up-regulation and/or to induce other suitable processes in the cells. This is expected to reduce the total energy or power delivered by the system and to mitigate effects on the non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning an electric field with the lengthwise or longer dimensions of the target cells, the electric field may propagate along the lateral or shorter dimensions of the non-target cells (i.e., such that the electric field propagates at least partially out of alignment with non-target smooth muscle cells SMC). Therefore, as seen in FIGS. 2A and 2B, applying an electric field with propagation lines Li generally aligned with the longitudinal dimension L of the artery A may preferentially cause electroporation (e.g., irreversible electroporation), electrofusion or other neuromodulation in cells of the target nerves N without unduly affecting the non-target arterial smooth muscle cells SMC. The electric field may propagate in a single plane along the longitudinal axis of the artery, or may propagate in the longitudinal direction along any angular segment θ through a range of 0°-360°.

An electric neuromodulation system placed within, through and/or in proximity to the wall of the artery may propagate an electric field having a longitudinal portion that is aligned to run with the longitudinal dimension of the artery in the region of the nerves N and the smooth muscle cells SMC of the vessel wall so that the wall of the artery remains at least substantially intact while the outer nerve cells are destroyed, fused or otherwise affected. Monitoring elements optionally may be utilized to assess an extent of, e.g., electroporation or temperature change, induced in nerves and/or in smooth muscle cells, as well as to adjust electric field parameters to achieve a desired effect.

C. Embodiments of Apparatus and Methods for Neuromodulation or Denervation

FIGS. 3-10 illustrate examples of intravascular systems and methods for neuromodulation or denervation. Applicants have previously described intravascular and intra-to-extravascular electric field systems for neuromodulation or denervation, for example, in co-pending U.S. patent application Ser. No. 11/129,765, filed May 13, 2005; and Ser. No. 11/363,867, filed on Feb. 27, 2006, both of which have been incorporated herein by reference. Furthermore, applicants have previously described thermal systems for neuromodulation or denervation, for example, in co-pending U.S. patent application Ser. No. 11/504,117, filed on Aug. 14, 2006, entitled Methods and Apparatus for Thermally-Induced Renal Neuromodulation.

Referring now to FIGS. 3A and 3B, an apparatus 300 for neuromodulation or denervation comprises a catheter 302 having an optional positioning element 304 (e.g., a balloon, an expandable wire basket, other mechanical expanders, etc.), shaft electrodes 306a and 306b positioned along the shaft of the catheter, and optional radiopaque markers 308 positioned along the shaft of the catheter in the region of the positioning element 304. The electrodes 306a-b, for example, can be arranged such that the electrode 306a is near a proximal end of the positioning element 304 and the electrode 306b is near the distal end of the positioning element 304. The electrodes 306 are electrically coupled to a field generator 50, which optionally may be positioned external to the patient, for delivery of an electric field to the target neural matter. In an alternative embodiment, one or more of the electrodes may comprise Peltier electrodes for heating or cooling the target neural matter to modulate the fibers or tissue.

The field generator 50, as well as any of the electrode embodiments described herein, may be utilized with any embodiment of the present invention for delivery of an electric field with desired field parameters. It should be understood that electrodes of embodiments described hereinafter may be electrically connected to the generator even though the generator is not explicitly shown or described with each embodiment. Furthermore, the field generator optionally may be positioned internal to the patient.

The positioning element 304 optionally may center or otherwise position the electrodes 306a and 306b within a vessel. Additionally, as in FIG. 3A, the positioning element may comprise an impedance-altering element that alters the impedance between the electrodes 306a and 306b during the therapy, for example, to better direct the electric field across the vessel wall. This may reduce an energy required to achieve desired neuromodulation or denervation and may reduce a risk of injury to non-target tissue. Applicants have previously described use of an impedance-altering element, for example, in co-pending U.S. patent application Ser. No. 11/266,993, filed Nov. 4, 2005, which is incorporated herein by reference in its entirety. When the positioning element 304 comprises an inflatable balloon, as in FIG. 3A, the balloon may serve as both a centering element for the electrodes 306 and as an impedance-altering electrical insulator for directing an electric field delivered across the electrodes, e.g., for directing the electric field into or across the vessel wall for modulation of target neural matter. Electrical insulation provided by the positioning element 304 may reduce the magnitude of applied energy or other parameters of the electric field necessary to achieve desired modulation of the target fibers, up to and including full denervation.

Furthermore, the positioning element 304 optionally may be utilized as a thermal element. For example, it may be inflated with a chilled fluid that serves as a heat sink for removing heat from tissue that contacts the element. Conversely, the positioning element 304 may be inflated with a warmed fluid that heats tissue in contact with the element. The thermal fluid within the element optionally may be circulated and/or exchanged within the positioning element 304 to facilitate more efficient conductive and/or convective heat transfer. Thermal fluids also may be used to achieve thermal neuromodulation via thermal cooling or heating mechanisms, as described in greater detail herein below. The positioning element 304, or any other portion of apparatus 300, additionally or alternatively may comprise one or more sensors for monitoring the temperature or other parameters of the target tissue, the non-target tissue, the electrodes, the positioning element, and/or any other portion of the apparatus 300 or of the patient's anatomy. The sensors, for example, can be a thermocouple 310 configured to contact the vessel wall (shown in FIG. 3A).

The positioning element optionally may comprise an eccentric positioning element. The eccentric positioning element may be configured, for example, to position the electrode(s) in contact with the vessel wall. For example, the electrode(s) may be coupled to the shaft of the catheter, and the eccentric positioning element may be expanded to bring the shaft of the catheter and the electrode(s) into contact with the vessel wall. The eccentric positioning element may comprise an eccentric balloon, an eccentric expandable basket, or any other eccentric positioning element.

The electrodes 306 can be individual electrodes (i.e., independent contacts), a segmented electrode with commonly connected contacts, or a single continuous electrode. Furthermore, the electrodes 306 may be configured to provide a bipolar signal, or the electrodes 306 may be used together or individually in conjunction with a separate patient ground pad for monopolar use. As an alternative or in addition to placement of the electrodes 306 along the central shaft of the catheter 302, as in FIG. 3, the electrodes 306 may be attached to the positioning element 304 such that they contact the wall of the renal artery RA. In such a variation, the electrodes may, for example, be affixed to the inside surface, outside surface or at least partially embedded within the wall of the positioning element. FIG. 4 illustrate alternative wall-contacting electrodes.

In use, the catheter 302 may be delivered to the artery A as shown, or it may be delivered to a vein or to any other vessel in proximity to target neural matter, in a low profile delivery configuration, for example, through a guide catheter. Alternatively, catheters may be positioned in multiple vessels for neuromodulation, e.g., within both an artery and a vein. Multi-vessel techniques for electric field neuromodulation have been described previously, for example, in Applicant's co-pending U.S. patent application Ser. No. 11/451,728, filed Jul. 12, 2006, which is incorporated herein by reference in its entirety.

Once positioned within the vasculature as desired, the optional positioning element 304 may be expanded into contact with an interior wall of the vessel. An electric field then may be generated by the field generator 50, transferred through the catheter 302 to the electrodes 306, and delivered via the electrodes 306 across the wall of the artery. The electric field modulates the activity along neural fibers within the wall of the artery or in proximity to the artery. The electrical field, for example, can at least partially denervate tissue or organ(s) innervated by the neural fibers. This may be achieved, for example, via ablation, non-ablative injury, or other changes to the target neural matter or supporting structures. The electric field additionally or alternatively may induce electroporation, e.g., irreversible electroporation, in the neural fibers, which also may contribute to the desired neuromodulation or denervation.

In the embodiment of FIG. 3A, the positioning element 304 illustratively comprises an inflatable balloon, which may preferentially direct the electric field as discussed. In the embodiment of FIG. 3B, the positioning element comprises an expandable wire basket that substantially centers the electrodes 306 within the vessel without blocking blood flow through the vessel. During delivery of the electric field (or of other energy), the blood may act as a thermal sink (either hot or cold) for conductive and/or convective heat transfer for removing excess thermal energy from the non-target tissue (such as the interior wall of the vessel), thereby protecting the non-target tissue. This effect may be enhanced when blood flow is not blocked during energy delivery, as in the embodiment of FIG. 3B.

Use of the patient's blood as a thermal sink is expected to facilitate delivery of longer or higher energy treatments with reduced risk of damage to the non-target tissue, which may enhance the efficacy of the treatment at the target neural matter. Although the embodiment of FIG. 3B illustratively comprises a positioning element that substantially centers the electrodes without significantly blocking flow, it should be understood that the positioning element may be eliminated and/or that the electrodes may be attached to the positioning element such that they are not centered in the vessel upon expansion of the positioning element. In such embodiments, the patient's blood may still remove excess heating or cooling thermal energy to protect non-target tissues.

In addition or as an alternative to utilizing the patient's blood as a thermal sink, a thermal fluid (hot or cold) may be injected into the vessel, e.g., upstream of, at, or through the energy delivery element, to remove excess thermal energy and protect the non-target tissues. The thermal fluid may, for example, be injected through the device catheter or through a guide catheter. Furthermore, this method of using an injected thermal fluid to remove excess thermal energy from non-target tissues to protect the non-target tissues from thermal injury during therapeutic treatment of target tissues may be utilized in body lumens other than blood vessels.

One or more sensors, such as the thermocouple 310 of FIG. 3A, may be used to monitor the temperature(s) or other parameter(s) at one or more locations. For example, the sensor(s) can monitor a parameter at the electrodes 306, the wall of the vessel, and/or other desired location of the apparatus or the patient's anatomy. The neuromodulation or denervation may be controlled using the measured parameter(s) as feedback. This feedback may be used, for example, to maintain the parameter(s) below a threshold that may cause injury to the non-target tissues or another desired threshold. Conversely, the feedback may be used to maintain the parameter(s) above a desired threshold, such as a threshold that may induce the desired neuromodulation or denervation. Furthermore, the feedback may be used to keep the parameter(s) within a range that will induce the desired neuromodulation or denervation without injuring or other producing undesirable results in the non-target tissues. Different parameters (or the same parameter at different locations) optionally may be used as control feedback for ensuring the desired effects while mitigating the undesired effects. With blood flowing through the vessel, more thermal energy may be carried away, which may allow for longer or higher energy treatments than when blood flow is blocked in the vessel.

As discussed, when utilizing intravascular apparatus to achieve neuromodulation or denervation, in addition, or as an alternative, to central positioning of the electrode(s) within a blood vessel, the electrode(s) optionally may be wall-contact electrodes configured to contact an internal wall of the blood vessel. Such wall-contacting electrode(s) may facilitate more efficient transfer of energy across the vessel wall to target neural fibers or tissue compared to centrally-positioned electrode(s). In some embodiments, the wall-contacting electrode(s) may be delivered to the vessel treatment site in a reduced profile configuration, then expanded in vivo to a deployed configuration wherein the electrode(s) contact the vessel wall. The expansion of the electrode(s) can be at least partially reversible to facilitate retrieval of the electrode(s) from the patient's vessel.

Figure 4A:
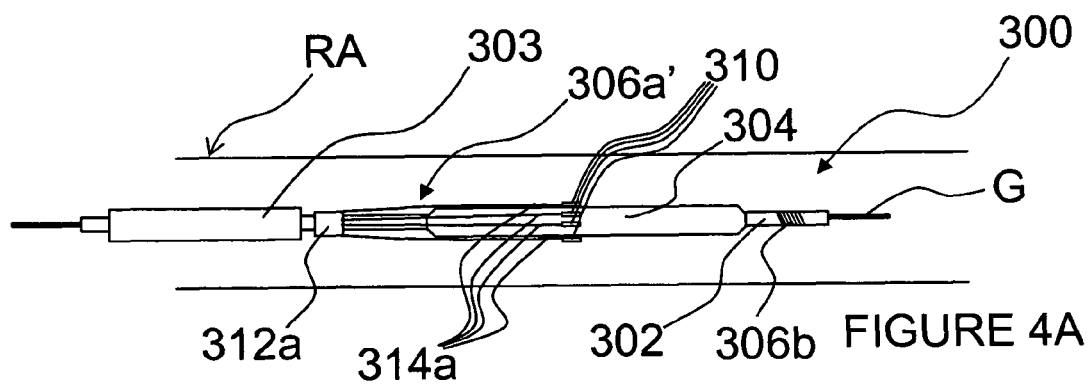
FIGS. 4A and 4B are schematic side views, partially in section, illustrating an alternative embodiment of the intravascular methods and apparatus of FIG. 3 comprising wall-contacting electrodes.
Figure 4B:
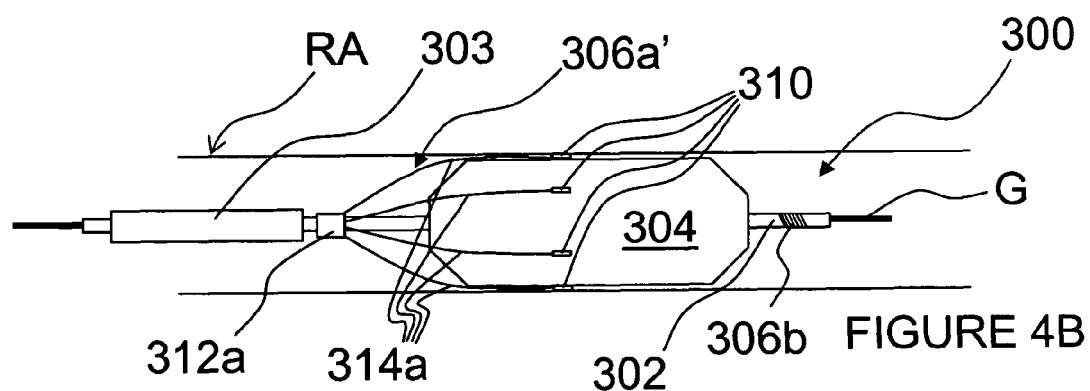

FIGS. 4A and 4B depict an illustrative embodiment of an intravascular apparatus having electrodes configured to contact the interior wall of a vessel. The apparatus of FIGS. 4A and 4B is an alternative embodiment of the apparatus 300 of FIGS. 3A and 3B wherein the proximal electrode 306a of FIGS. 3A and 3B has been replaced with wall-contact electrode 306a'. The wall-contact electrode 306a' comprises a proximal attachment 312a that connects the electrode to the shaft of the catheter 302 and is electrically coupled to the generator. One or more extensions 314a extend from proximal attachment 312a and at least partially extend over a surface of the positioning element 304. The extensions 314a may be selectively insulated such that only an assigned portion of the extensions, e.g., the distal tips of the extensions, are electrically active. One or more thermocouples 310 optionally may be provided in proximity to the electrically active portions of the electrodes for monitoring the temperature of the active portions or of tissue in contact with the active portions. The wall-contact electrode 306a' may be fabricated from a slotted tube, such as a stainless steel or shape-memory (e.g., NiTi) slotted tube. Furthermore, all or a portion of the electrode may be gold-plated to improve radiopacity and/or conductivity.

As seen in FIG. 4A, the catheter 302 may be delivered over a guidewire G to a treatment site within the patient's vessel with the wall-contact electrode 306a' positioned in a reduced profile configuration. The catheter 302 optionally may be delivered through a guide catheter or other sheath 303 to facilitate such reduced profile delivery of the wall-contacting electrode. When positioned as desired at a treatment site, the wall-contact electrode 306a may be expanded into contact with the vessel wall by expanding the positioning element 304 (shown in FIG. 4B). A monopolar or bipolar electric field then may be delivered across the vessel wall, e.g., a bipolar electric field between the electrodes 306a' and 306b, to induce the neuromodulation or denervation, as discussed previously. The optional positioning element 304 may alter impedance within the blood vessel and more efficiently route the electrical energy across the vessel wall to the target neural fibers or tissue.

After delivery of the electric field, the wall-contact electrode 306a' may be returned to a reduced profile to facilitate removal of the apparatus 300 from the patient. For example, the positioning element 304 may be collapsed (e.g., deflated), and the wall-contact electrode 306a' may be re-collapsed by withdrawing the catheter 302 within the guide catheter 303. Alternatively, the electrode may be fabricated from a shape-memory material biased to the collapsed configuration, such that the electrode self-collapses upon collapse of the positioning element.

The wall-contact electrode 306a' or the electrode 306b optionally may be utilized in a monopolar fashion in combination with an external electrode or other remote electrode (not shown) to achieve the desired neuromodulation or denervation. When either the wall-contact electrode 306a' or the electrode 306b is utilized in a monopolar fashion, the other electrode optionally may be eliminated. Alternatively, the other electrode may not be electrically activated during treatment. As another alternative, both electrodes may be activated with the same polarity and used in combination with a remote electrode to achieve a monopolar neuromodulation or denervation.

Figure 5A:
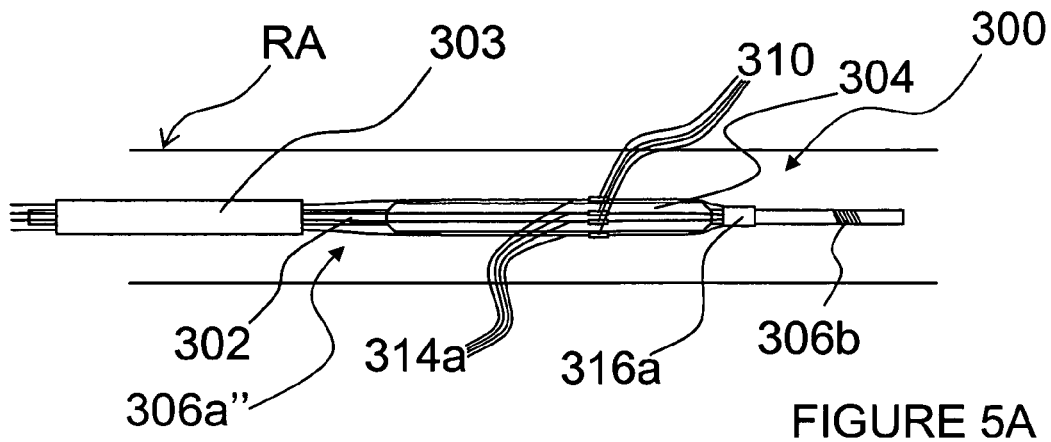
FIGS. 5A and 5B are schematic side views, partially in section, illustrating an additional alternative embodiment of the intravascular methods and apparatus of FIG. 3 comprising alternative wall-contacting electrodes.
Figure 5B:
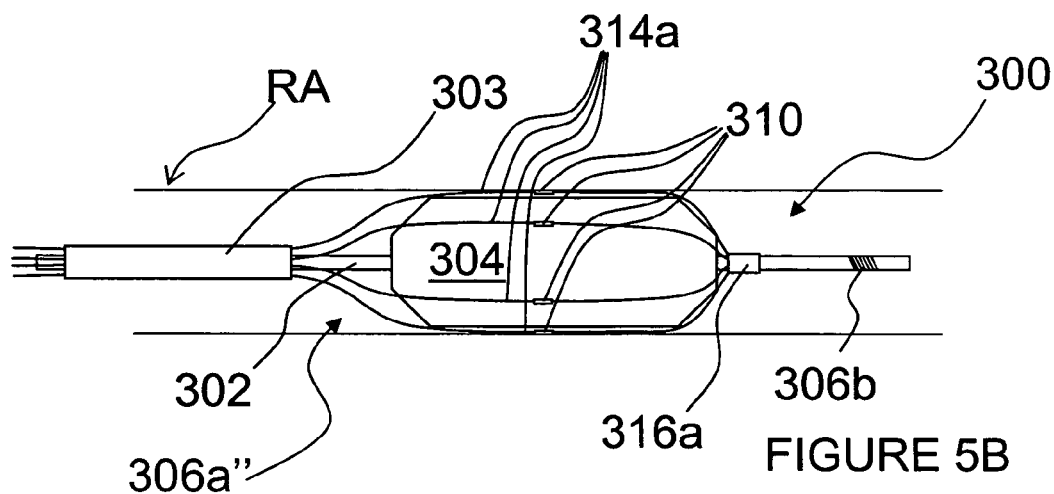

FIGS. 5A and 5B depict another embodiment of the apparatus and methods of FIGS. 3A and 3B comprising a wall-contact electrode. As an alternative to the proximal attachment 312a of the wall-contact electrode 306a' of FIGS. 4A and 4B, the electrode 306a'' of FIGS. 5A and 5B comprises distal attachment 316a for coupling the electrode to the shaft of catheter 302 on the distal side of the positioning element 304. Distal attachment of the electrode allows the electrode to extend over the entirety of the positioning element 304 and may facilitate re-collapse of the electrode 306a'' after the neuromodulation or denervation. Re-collapse may be achieved, for example, by proximally retracting the extensions 312a relative to the catheter 302 during or after re-collapse of the positioning element 304. FIG. 5A shows the electrode 306a'' in the reduced profile configuration, while FIG. 5B shows the electrode in the expanded, wall-contacting configuration.

Figure 6A:
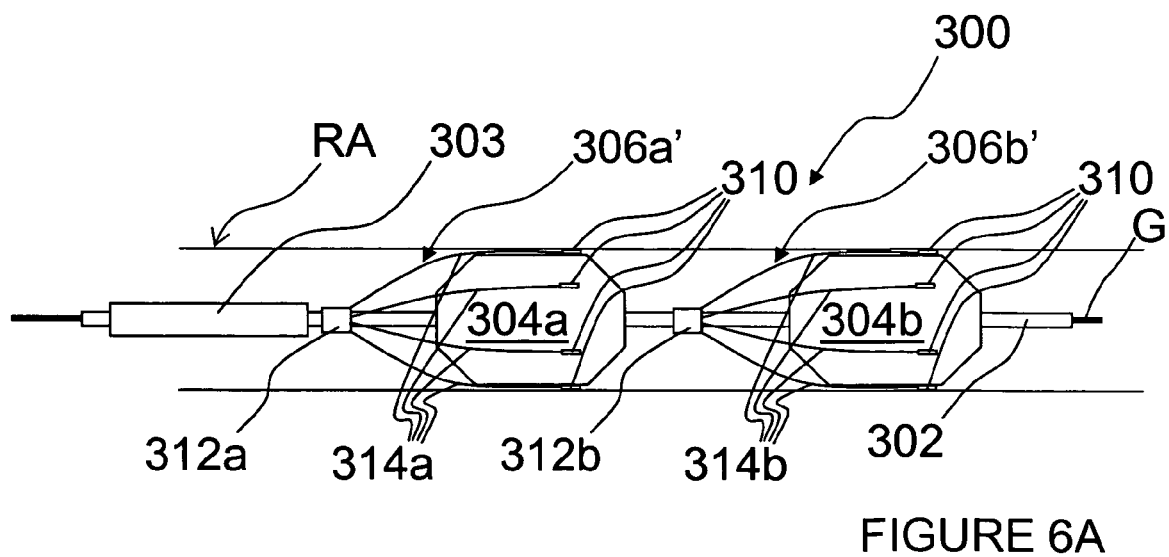
FIGS. 6A and 6B are schematic side views, partially in section, illustrating other alternative embodiments of the intravascular methods and apparatus of FIG. 3 comprising multiple wall-contacting electrodes.
Figure 6B:
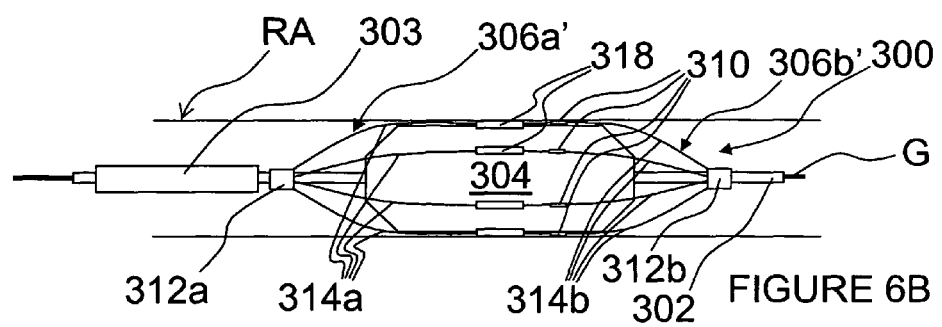

FIGS. 6A and 6B show additional alternative embodiments of the methods and apparatus of FIGS. 3A and 3B. In FIGS. 6A and 6B, the apparatus 300 comprises both the proximal wall-contact electrode 306a' of FIGS. 4A and 4B, as well as a wall-contact distal electrode 306b'. The embodiment of FIG. 6A comprises proximal and distal positioning elements 304a and 304b, respectively, for expanding the proximal and distal wall-contact electrodes 306a' and 306b', respectively, into contact with the vessel wall. The embodiment of FIG. 6B comprises only a single positioning element 304, but the distal wall-contact electrode 306b' is proximal facing and positioned over the distal portion of the positioning element 304 to facilitate expansion of the distal electrode 306b'. In the embodiment of FIG. 6B, the extensions of the proximal and distal wall-contact electrodes optionally may be connected along non-conductive connectors 318 to facilitate collapse and retrieval of the electrodes post-treatment.

A bipolar electric field may be delivered between the proximal and distal wall-contact electrodes, or a monopolar electric field may be delivered between the proximal and/or distal electrode(s) and a remote electrode. Having both the proximal and distal wall-contact electrodes in contact with the wall of the vessel may facilitate more efficient energy transfer across the wall during delivery of an electric field, as compared to having one or both of the proximal and distal electrodes centered within the vessel.

In addition to intravascular systems for neuromodulation or denervation, intra-to-extravascular systems may be provided. The intra-to-extravascular systems may, for example, have electrode(s) or other energy delivery element(s) that are delivered to an intravascular position, and then at least partially passed through/across the vessel wall to an extravascular position prior to delivery of energy. Intra-to-extravascular positioning of the element(s) may place the element(s) in closer proximity to target neural fibers or tissue for delivery of energy, as compared to fully intravascular positioning of the element(s).

Figure 7:
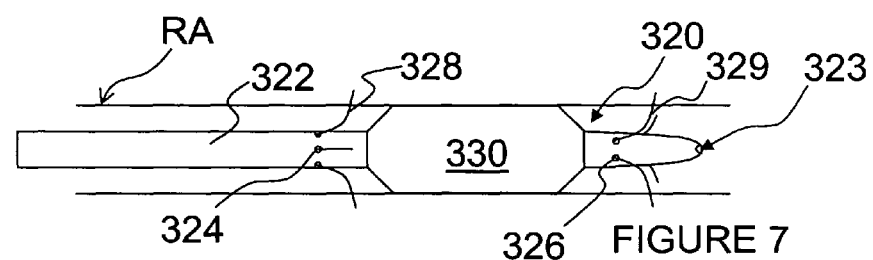
FIG. 7 is a schematic side view, partially in section, illustrating an example of an intra-to-extravascular method and apparatus for neuromodulation or denervation.

With reference to FIG. 7, one embodiment of an intra-to-extravascular ("ITEV") system 320 comprises a catheter 322 having (a) a plurality of proximal electrode lumens terminating at proximal side ports 324, (b) a plurality of distal electrode lumens terminating at distal side ports 326, and (c) a guidewire lumen 323. The catheter 322 preferably comprises an equal number of proximal and distal electrode lumens and side ports. The system 320 also includes proximal needle electrodes 328 that may be advanced through the proximal electrode lumens and the proximal side ports 324, as well as distal needle electrodes 329 that may be advanced through the distal electrode lumens and the distal side ports 326.

The catheter 322 comprises an optional expandable positioning element 330, which may comprise an inflatable balloon or an expandable basket or cage. In use, the positioning element 330 may be expanded prior to deployment of the needle electrodes 328 and/or 329 in order to position or center the catheter 322 within the patient's vessel (e.g., within artery A). Centering the catheter 322 is expected to facilitate delivery of all needle electrodes to desired depths within/external to the patient's vessel (e.g., to deliver all of the needle electrodes approximately to the same depth). In FIG. 7, the illustrated positioning element 330 is positioned between the proximal side ports 324 and the distal side ports 326, i.e., between the delivery positions of the proximal and distal electrodes. However, it should be understood that the positioning element 330 additionally or alternatively may be positioned at a different location or at multiple locations along the length of the catheter 322 (e.g., at a location proximal of the side ports 324 and/or at a location distal of the side ports 326).

As illustrated in FIG. 7, the catheter 322 may be advanced to a treatment site within the patient's vasculature (e.g., to a treatment site within the patient's artery A) over a guidewire (not shown) via the lumen 323. During intravascular delivery, the electrodes 328 and 329 may be positioned such that their non-insulated and sharpened distal regions are positioned within the proximal and distal lumens, respectively. Once positioned at a treatment site, a medical practitioner may advance the electrodes via their proximal regions that are located external to the patient. Such advancement causes the distal regions of the electrodes 328 and 329 to exit side ports 324 and 326, respectively, and pierce the wall of the patient's vasculature such that the electrodes are positioned extravascularly via an ITEV approach.

The proximal electrodes 328 can be connected to field generator 50 as active electrodes, and the distal electrodes 329 can serve as return electrodes. In this manner, the proximal and distal electrodes form bipolar electrode pairs that align an electric field with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Furtherstill, the proximal and/or the distal electrodes may be utilized in combination with an external ground for delivery of a monopolar thermal electric field. Any combination of active and distal electrodes may be utilized, as desired.

When the electrodes 328 and 329 are connected to generator 50 and positioned extravascularly, and with the positioning element 330 optionally expanded, delivery of an electric field may proceed to achieve desired neuromodulation or denervation. The electric field, for example, may induce irreversible electroporation and/or thermal damage. After achievement of the neuromodulation or denervation, the electrodes may be retracted within the proximal and distal lumens, and the positioning element 330 may be collapsed for retrieval. ITEV system 320 then may be removed from the patient to complete the procedure. Additionally or alternatively, the system may be repositioned to provide therapy at another treatment site.

As discussed previously, protective elements, such as convective thermal elements, may be utilized to protect non-target tissues like smooth muscle cells from damage during neuromodulation or denervation. Non-target tissues additionally or alternatively may be protected by focusing energy on the target neural fibers or tissue, such that an intensity of the energy is insufficient to induce damage in the non-target tissues distant from the target neural fibers or tissue.

Although FIGS. 2-7 illustratively show bipolar apparatus, it should be understood that monopolar apparatus alternatively may be utilized. For example, an active monopolar electrode may be positioned intravascularly or intra-to-extravascularly in proximity to target neural matter. A remote electrode may be attached to the exterior of the patient. Finally, an electric field may be delivered between the in vivo monopolar electrode and an ex vivo remote electrode to effectuate desired neuromodulation or denervation. When utilizing monopolar apparatus, only a single electrode optionally may be provided.

The embodiments of FIGS. 2-7 illustratively describe methods and apparatus for neuromodulation or denervation via delivery of electric fields to the target neural fibers or tissue. However, it should be understood that alternative methods and apparatus for neuromodulation may be provided. For example, thermally-induced neuromodulation or denervation optionally may be achieved via application of thermal energy to the target neural fibers or other neural tissue. Thermal energy may be generated and/or transferred in a variety of ways, such as via conduction, convection or radiation; via delivery of a heated or chilled fluid; via a thermoelectric or Peltier element; via resistive heating induced by an electric field, via magnetic or electromagnetic techniques, etc. Thermally-induced neuromodulation or denervation additionally or alternatively may be achieved via application of high-intensity focused ultrasound to the target neural matter. Additional and alternative methods and apparatus for neuromodulation or denervation may be used in accordance with the present invention.

Although the wall-contacting and intra-to-extravascular electrodes of FIGS. 4-7 illustratively comprise multiple extensions, electrodes or needles at each laterally-positioned treatment location, it should be understood that a single extension/electrode/needle optionally may be provided at each laterally-positioned treatment location. Alternatively, multiple extensions or electrodes may be provided at the treatment location(s), but may be spaced unevenly about the circumference of the vessel. In this manner, an eccentric treatment, e.g., a non-circumferential and/or focal treatment, may be applied to the vessel. An eccentric or unitary treatment may reduce a risk of acute or late stenosis formation within the vessel, as compared to a full circumferential treatment.

Although the wall-contacting and intra-to-extravascular electrodes of FIGS. 4-7 illustratively are expanded via positioning elements, it should be understood that the electrodes in accordance with the present invention additionally or alternatively may be configured to self-expand into contact with the vessel wall. For example, the electrodes may self-expand after removal of a sheath or guide catheter constraining the electrodes in a reduced delivery configuration. The electrodes may, for example, be fabricated from (or coupled to) shape-memory elements that are configured to self-expand. Self-expanding embodiments optionally may be collapsed for retrieval from the patient by re-positioning of a constraining sheath or catheter over the self-expanding electrodes.

Figure 8:
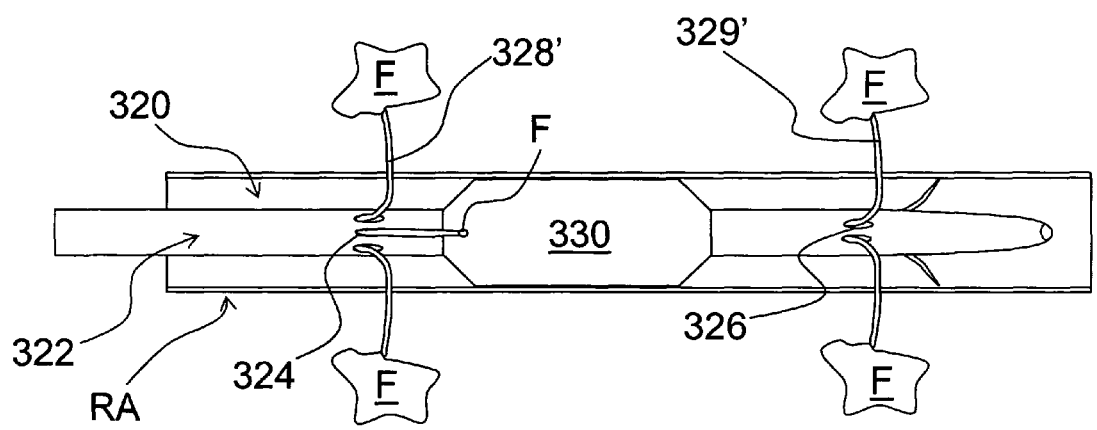
FIG. 8 is a schematic side view, partially in section, of an alternative embodiment of the method and apparatus of FIG. 7 configured for neuromodulation or denervation via injection of a neuromodulatory substance and/or of a thermal fluid.

With reference now to FIG. 8, an alternative embodiment of the apparatus and methods of FIG. 7 is described, which may be used for thermally-induced neuromodulation via direct application of thermal energy. In the embodiment of FIG. 8, the electrodes 328 and 329 of FIG. 7 have been replaced with infusion needles 328' and 329', respectively. A fluid F, such as a thermal fluid, may be delivered through the needles to the target neural matter. The thermal fluid, e.g., steam, may be heated in order to raise the temperature of the target neural matter above a desired threshold, for example, above a body temperature of about 37° C. or above a temperature of about 45° C. Alternatively, the thermal fluid may be chilled to reduce the temperature of the target neural matter below a desired threshold, for example, below the body temperature of about 37° C., below about 20° C., or below a freezing temperature of about 0° C. As will be apparent, in addition to intra-to-extravascular delivery of a thermal fluid, the thermal fluid may be delivered intravascularly (e.g., may inflate and/or be circulated through a balloon member), extravascularly (e.g., may be circulated through a vascular cuff) or a combination thereof.

In addition or as alternative to injection of a thermal fluid to the target neural matter through the infusion needles 328' and 329', an alternative fluid F, such as a neuromodulatory agent (e.g., a drug or medicament), may be injected, for example, to modulate, necrose or otherwise block or reduce transmission along the target neural matter. Examples of neuromodulatory agents include, but are not limited to, phenol; neurotoxins, such as botulinum toxin; beta blockers; vasodilators; and/or other standard heart failure drugs, renal drugs, or cardio-renal drugs. Additional neuromodulatory agents, per se known, will be apparent to those of skill in the art.

As an alternative to laterally spaced injection of a fluid, such as a thermal fluid or neuromodulatory agent, the fluid F optionally may be injected a single longitudinal location, i.e., along a single cross-section of the vessel. For example, the fluid may be injected only through the infusion needles 328' or only through the infusion needles 329'. When utilizing such a method of treatment, the needles 328' or the needles 329' may be eliminated.

Optionally, only a single infusion needle 328' and/or a single infusion needle 329' may be provided. Alternatively, an eccentric spacing of the infusion needles 328' and/or the infusion needles 329' may be provided. Treatment utilizing such embodiments may reduce a risk of acute or late stenosis formation, as compared to full circumferential treatment.

Figure 9A:
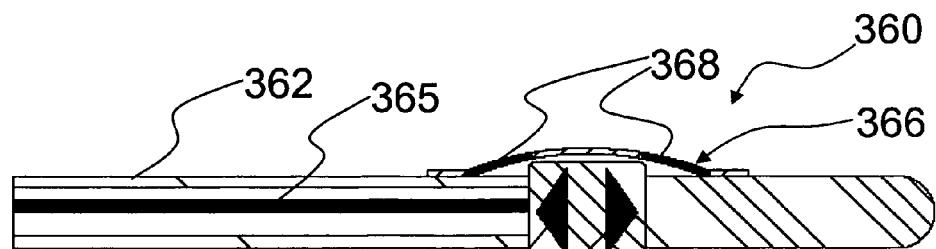
FIGS. 9A and 9B are schematic side views, partially in section, illustrating a method and apparatus for neuromodulation or denervation via high-intensity focused ultrasound.
Figure 9B:
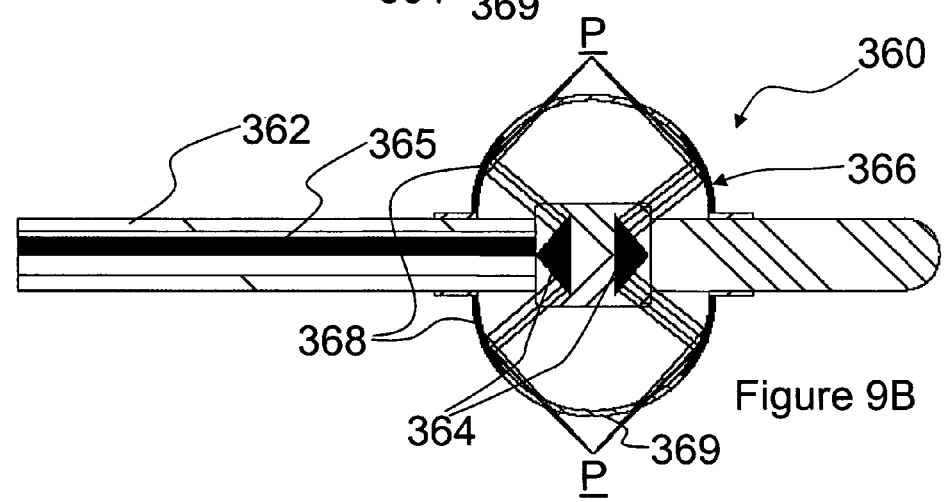

Intravascularly-induced neuromodulation alternatively may be achieved via high-intensity focused ultrasound, either pulsed or continuous. High intensity focused ultrasound may induce thermal injury and/or reversible or irreversible electroporation in the target neural matter. Furthermore, the ultrasound may be delivered over a full 360° (e.g. when delivered intravascularly) or over a radial segment of less than 360° (e.g., when delivered intravascularly, extravascularly, intra-to-extravascularly, or a combination thereof). In FIGS. 9A and 9B, the apparatus 360 comprises a catheter 362 having ultrasound transducers 364 positioned along the shaft of the catheter within an inflatable balloon 366. The ultrasound transducers are coupled to an ultrasound signal generator via conductors 365. The balloon comprises an acoustically reflective portion 368 of a surface of the balloon for reflecting an ultrasound wave, as well as an acoustically transmissive portion 369 of the surface for passage of the wave through the balloon. In this manner, the wave may be focused as shown at a focal point or radius P positioned a desired focal distance from the catheter shaft. In an alternative embodiment, the transducers may be attached directly to the balloon.

The focal distance may be specified or dynamically variable such that, when positioned within a blood vessel, the ultrasonic wave is focused at a desired depth on target neural matter outside of the vessel. For example, a family of catheter sizes may be provided to allow for a range of specified focal distances. A dynamically variable focal distance may be achieved, for example, via calibrated expansion of the balloon.

Figure 10:
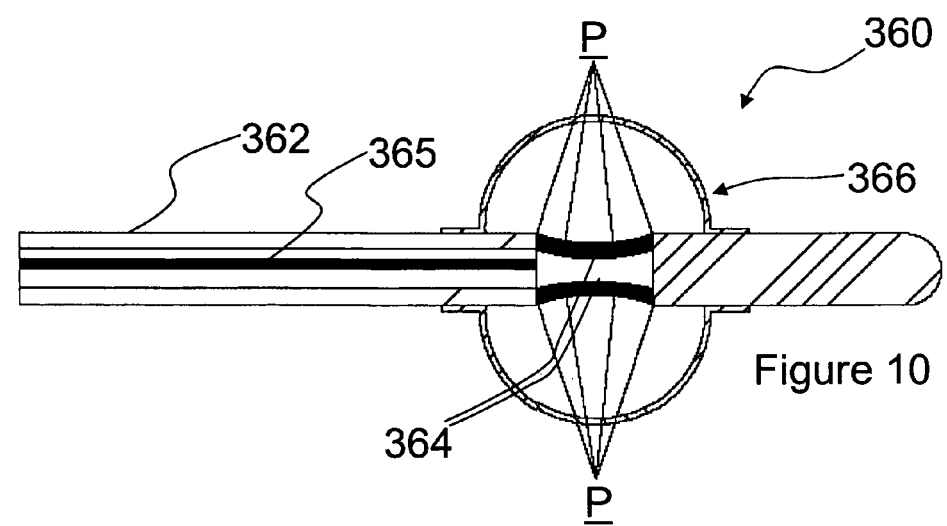
FIG. 10 is a schematic side view, partially in section, illustrating an alternative embodiment of the apparatus and method of FIG. 9.

Focusing the ultrasound wave may protect the non-target tissues and selectively affect the target neural matter to achieve neuromodulation via heating. FIG. 9A shows the apparatus 360 in a reduced delivery and retrieval configuration, while FIG. 9B shows the apparatus in an expanded deployed configuration. FIG. 10 shows an alternative embodiment of the apparatus 360 wherein the ultrasound transducers 364' are concave, such that the ultrasound signal is self-focusing without need of the reflective portion of the balloon 366 (e.g., the balloon may be acoustically transmissive at all points).

The apparatus described above with respect to FIGS. 3-10 optionally may be used to quantify the efficacy, extent or cell selectivity of neuromodulation in order to monitor and/or control the neuromodulation. As discussed previously, the apparatus may further comprise one or more sensors, such as thermocouples or imaging transducers, for measuring and monitoring one or more parameters of the apparatus, of the target neural matter, and/or of the non-target tissues. For example, a temperature rise or drop above or below certain thresholds may thermally ablate, non-ablatively injure, freeze or otherwise damage the target neural matter, thereby modulating the target neural fibers or neural tissue.

It is expected that intravascularly-induced neuromodulation may alleviate clinical symptoms of several neurological disorders or other medical conditions for an extended period of time, potentially up to six months or more. This time period may be sufficient to allow the body to heal, thereby alleviating a need for subsequent re-treatment. Alternatively, as symptoms re-occur, or at regularly scheduled intervals, the patient may receive repeat therapy.

Although preferred illustrative variations of the present invention are described above, it will be apparent to those skilled in the art that various changes and modifications may be made thereto without departing from the invention. It is intended in the appended claims to cover all such changes and modifications that fall within the true spirit and scope of the invention.

We claim:

1. A device for renal neuromodulation, the device being sized and shaped for placement within a renal blood vessel of a human patient, the device comprising:
 a neuromodulation element,
  wherein the device is configured to be connected to a controller for selectively delivering stimulation parameters to the neuromodulation element for application within the renal blood vessel,
  wherein the neuromodulation element is configured to contact, but not pass through, a wall of the renal blood vessel in proximity to a target neural matter that innervates a kidney of the patient,
  wherein the neuro modulation element is configured to deliver sufficient electrical energy from within the renal blood vessel to inhibit neural activity across the target neural matter, and
  wherein the device is further configured to deliver a cooling fluid at or through the neuromodulation element to remove excess thermal energy and protect non-target tissues.

2. The device of claim 1, wherein the neuromodulation element is configured to deliver an electric field relative to the target neural matter.

3. The device of claim 1, further comprising at least one sensor carried by the device.

4. The device of claim 3, further comprising a feedback control in communication with the sensor.

5. The device of claim 1, wherein the neuromodulation element further comprises at least one thermal element configured to deliver thermal energy relative to the target neural matter.

6. The device of claim 1, wherein neuromodulation element comprises a wall-contact electrode.

7. The device of claim 6, wherein the wall-contact electrode comprises a monopolar electrode.

8. The device of claim 6, wherein the wall-contact electrode is configured to deliver RF energy to the target neural matter adjacent the wall of the renal blood vessel.

9. The device of claim 6, wherein the wall-contact electrode is configured to ablate the target neural matter.

10. The device of claim 1 wherein the neuromodulation element is carried by a positioning element at a distal portion of the device, and wherein the positioning element is transformable between a low-profile, delivery configuration and a deployed configuration sized and shaped to fit within the renal blood vessel, and wherein, in the deployed configuration, the positioning element is configured to place the neuromodulation element in apposition with the wall of the renal blood vessel.

11. The device of claim 10 wherein the positioning element is configured to self-expand from the low-profile, delivery configuration to the deployed configuration.

12. The device of claim 1 wherein the neuromodulation element comprises a first neuromodulation element, and wherein the device further comprises at least a second neuromodulation element.

13. The device of claim 1, further comprising a helical section at a distal portion of the device and sized and shaped for placement within the renal blood vessel of the patient, and wherein:
 the neuromodulation element is carried by the helical section; and
 the helical section is transformable between a low-profile delivery configuration for intravascular placement within the renal blood vessel and an expanded treatment configuration, and
 wherein, in the expanded treatment configuration, the helical section is adapted to bring the neuromodulation element into contact with the wall of the renal blood vessel.

14. The device of claim 13 wherein the helical section is configured to self expand from the delivery configuration to the treatment configuration.

15. The device of claim 1 wherein the device is configured for placement in the renal blood vessel over a guidewire.

* * * * *